US010352920B2

(12) United States Patent
Ehrenkranz

(10) Patent No.: US 10,352,920 B2
(45) Date of Patent: Jul. 16, 2019

(54) SUPPLEMENTS AND MONITORING SYSTEMS FOR DOSING OF THE SUPPLEMENTS

(71) Applicant: i-CalQ, LLC, Salt Lake City, UT (US)

(72) Inventor: Joel R. L. Ehrenkranz, Salt Lake City, UT (US)

(73) Assignee: i-calQ, LLC, Salt Lake City ( * ) Notice: Subject to any disclaimer, the term of this patent is extended or adjusted under 35 U.S.C. 154(b) by 0 days.

(21) Appl. No.: 14/654,774

(22) PCT Filed: Dec. 20, 2013

(86) PCT No.: PCT/US2013/077217
§ 371 (c)(1),
(2) Date: Jun. 22, 2015

(87) PCT Pub. No.: WO2014/100715
PCT Pub. Date: Jun. 26, 2014

(65) Prior Publication Data
US 2015/0338387 A1    Nov. 26, 2015

Related U.S. Application Data

(60) Provisional application No. 61/740,979, filed on Dec. 21, 2012, provisional application No. 61/745,240, (Continued)

(51) Int. Cl.
*G01N 33/53*     (2006.01)
*G01N 33/52*     (2006.01)
(Continued)

(52) U.S. Cl.
CPC ......... *G01N 33/487* (2013.01); *A61B 5/1455* (2013.01); *A61B 5/6898* (2013.01);
(Continued)

(58) Field of Classification Search
None
See application file for complete search history.

(56) References Cited

U.S. PATENT DOCUMENTS 4,888,414 A * 12/1989 Knutson .................. C07K 7/06
530/303
5,200,345 A * 4/1993 Young .................... G01N 33/48
324/317
(Continued)

OTHER PUBLICATIONS

Moses King James Bible Genesis 24 Verses 1-20 (publication year 1611).*
(Continued)

*Primary Examiner* — Changhwa J Cheu
(74) *Attorney, Agent, or Firm* — Magleby Cataxinos & Greenwood

(57) ABSTRACT

Methods for monitoring and adjusting a physiological state of a subject. The methods include (1) providing a subject having one or more physiological parameters defined by one or more biometrics, (2) monitoring a selected biometric analyte associated with a selected biometric to define a state of the selected biometric, (3) based on the results of the monitoring, adjusting the state of the selected biometric by administering to the subject a supplement selected to affect the state of the selected biometric.

5 Claims, 8 Drawing Sheets

Related U.S. Application Data filed on Dec. 21, 2012, provisional application No. 61/910,749, filed on Dec. 2, 2013.

(51) Int. Cl.

| | | |
|---|---|---|
| *G01N 33/487* | (2006.01) | |
| *G01N 33/543* | (2006.01) | |
| *A61K 35/60* | (2006.01) | |
| *A61K 33/26* | (2006.01) | |
| *A61K 36/889* | (2006.01) | |
| *A61K 31/12* | (2006.01) | |
| *A61K 36/906* | (2006.01) | |
| *A61K 31/59* | (2006.01) | |
| *A61K 33/18* | (2006.01) | |
| *A61K 31/522* | (2006.01) | |
| *G01N 21/17* | (2006.01) | |
| *G01N 33/49* | (2006.01) | |
| *A61N 5/06* | (2006.01) | |
| *A61B 5/00* | (2006.01) | |
| *A61B 5/1455* | (2006.01) | |
| *G01N 33/50* | (2006.01) | |
| *G01N 21/84* | (2006.01) | |
| *G01N 33/558* | (2006.01) | |
| *A61B 5/145* | (2006.01) | |
| *G06F 19/00* | (2018.01) | |

(52) U.S. Cl.
CPC .......... *A61K 31/12* (2013.01); *A61K 31/522* (2013.01); *A61K 31/59* (2013.01); *A61K 33/18* (2013.01); *A61K 33/26* (2013.01); *A61K 35/60* (2013.01); *A61K 36/889* (2013.01); *A61K 36/906* (2013.01); *A61N 5/062* (2013.01); *G01N 21/17* (2013.01); *G01N 21/8483* (2013.01); *G01N 33/49* (2013.01); *G01N 33/50* (2013.01); *G01N 33/52* (2013.01); *G01N 33/54366* (2013.01); *G01N 33/558* (2013.01); *A23V 2002/00* (2013.01); *A61B 5/14507* (2013.01); *A61B 2560/0443* (2013.01); *G01N 2021/1765* (2013.01); *G06F 19/3475* (2013.01); *Y02A 90/26* (2018.01)

(56) References Cited

U.S. PATENT DOCUMENTS

| | | | | |
|---|---|---|---|---|
| 6,521,247 | B1 * | 2/2003 | deVries | A23L 33/15 424/439 |
| 7,371,582 | B2 * | 5/2008 | Nahm | B01L 3/5023 422/504 |
| 8,771,962 | B2 * | 7/2014 | Southern | G01N 33/528 435/7.1 |
| 8,889,424 | B2 * | 11/2014 | Ehrenkranz | G01N 21/49 422/425 |
| 2006/0240015 | A1 * | 10/2006 | Shitara | C07K 16/2896 424/145.1 |
| 2007/0031286 | A1 * | 2/2007 | Miike | G01N 33/543 422/68.1 |
| 2011/0015154 | A1 | 1/2011 | Kellermann et al. | |
| 2011/0202033 | A1 | 8/2011 | Welsleder et al. | |
| 2011/0257117 | A1 | 10/2011 | Matt et al. | |
| 2012/0035061 | A1 * | 2/2012 | Bransky | G01N 15/147 506/7 |
| 2012/0201747 | A1 | 8/2012 | Altschul et al. | |
| 2013/0134293 | A1 * | 5/2013 | Neijzen | G01J 3/02 250/201.1 |
| 2015/0031581 | A1 * | 1/2015 | Kema | G01N 33/6848 506/12 |

OTHER PUBLICATIONS

Vincent et al. Metabolism 2009 vol. 58, p. 254-262 (Year: 2009).*
Head et al., Nutrients and botanicals for treatment of stress: adrenal fatigue, neurotransmitter imbalance, anxiety, and restless sleep, Alternative Medicine Review: a Journal of Clinical Therapeutic, 2009, vol. 14(2), pp. 114-140. p. 122-123, p. 122, col. 2, par 2.
Schult et al., Effects of powdered fertilized eggs on the stress response, Clinical Nutrition, 2010, vol. 29, pp. 255-260, summary, p. 256, para 2.2, 2.3, p. 257, para 3.11, p. 259, col. 2, para 2.
Oben et al., The effect of Cissus quadrangularis (CQR-300) and a Cissus formulation (CORE) on obesity and obesity-induced oxidative stress, Lipids in Health and Disease, Feb. 4, 2007, vol. 6(4), pp. 1-8. p. 1, p. 3, Table 4; p. 4, col. 1, para 4.
PCT/US2013/077217, dated Jul. 29, 2014, International Search Report and Written Opnion.

* cited by examiner

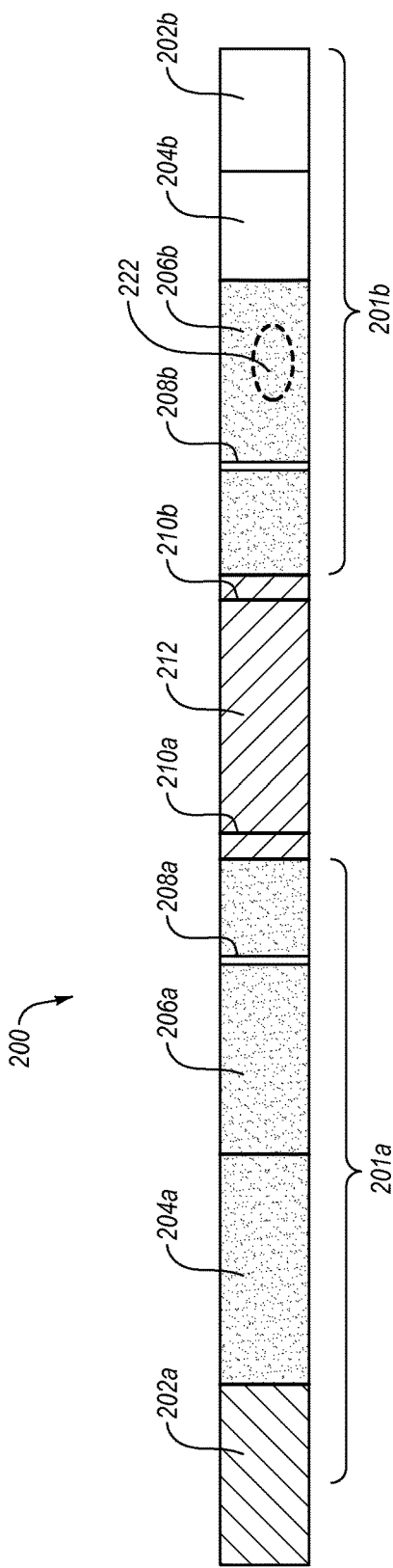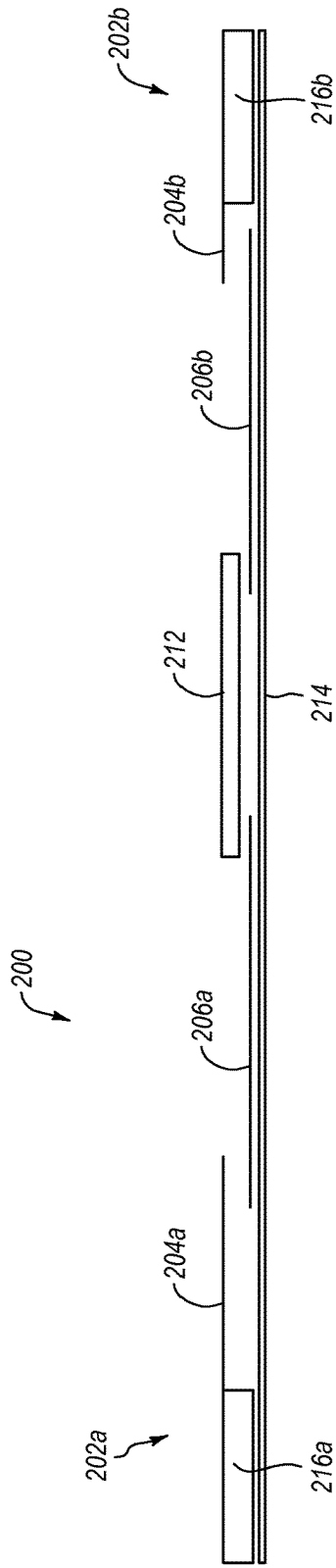

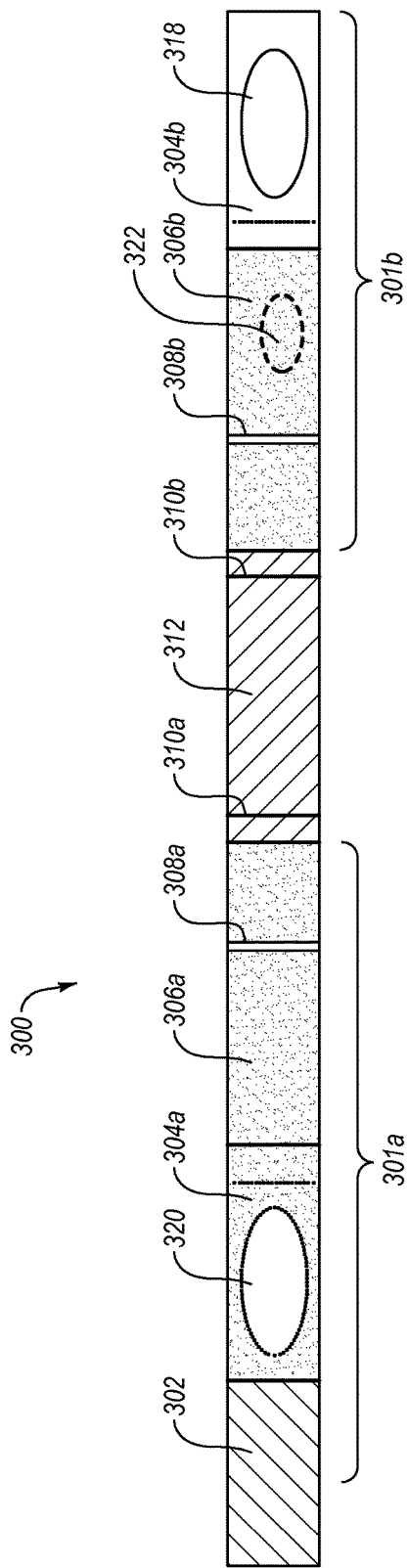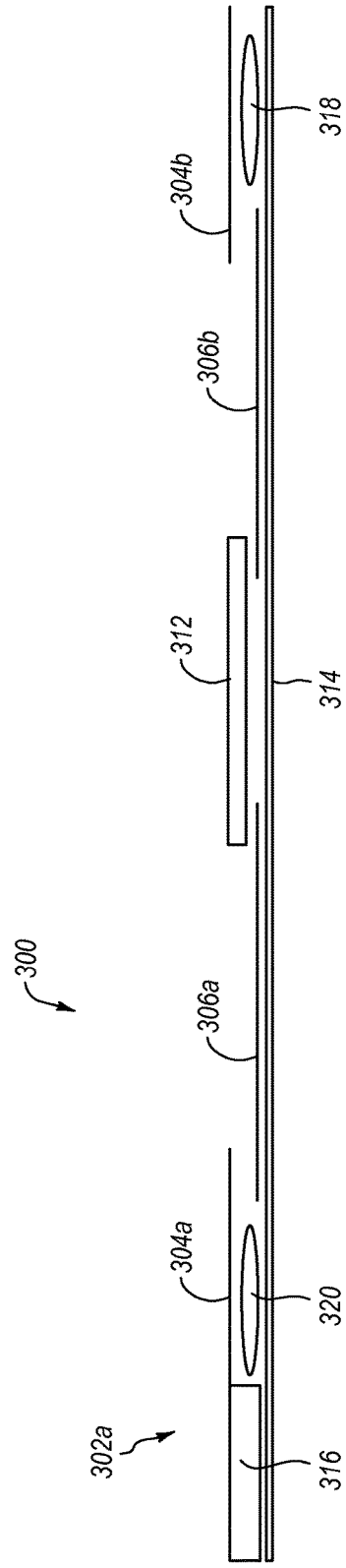

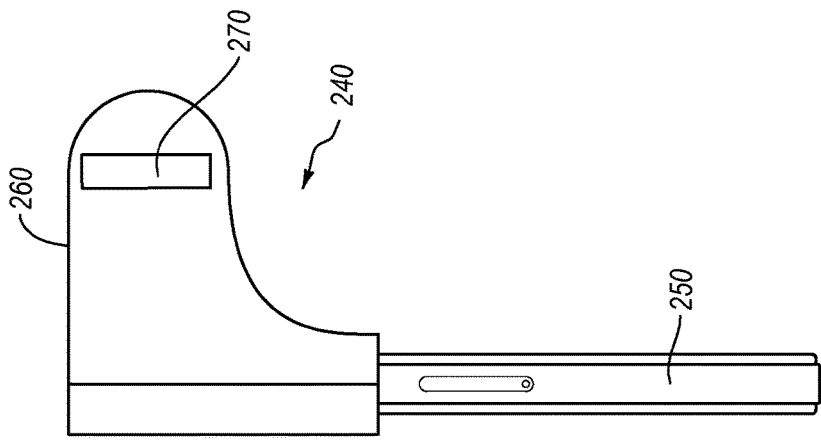
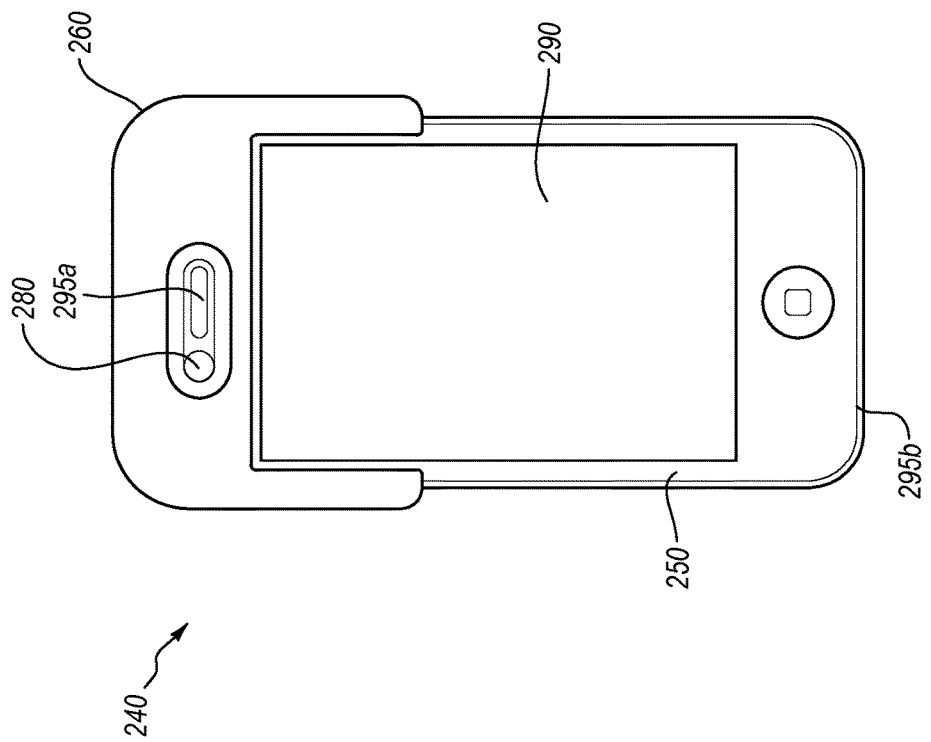

SUPPLEMENTS AND MONITORING SYSTEMS FOR DOSING OF THE SUPPLEMENTS

CROSS-REFERENCE TO RELATED APPLICATIONS

This application is a U.S. Nationalization of PCT Application Number PCT/US2013/077217, filed on Dec. 20, 2013, which claims the benefit of and priority to U.S. Prov. Pat. App. Ser. No. 61/745,240 filed 21 Dec. 2012, U.S. Prov. Pat. App. Ser. No. 61/910,749 filed 2 Dec. 2013, and U.S. Prov. Pat. App. Ser. No. 61 /740,979 filed 21 Dec. 2012, the entireties of which are incorporated herein by reference.

BACKGROUND

A dietary supplement, also known as food supplement or nutritional supplement, is a preparation intended to supplement the diet and provide nutrients, such as vitamins, minerals, fiber, fatty acids, or amino acids, that may be missing or may not be consumed in sufficient quantities in a person's diet. In the United States, over $20 billion worth of dietary supplements are sold every year; energy drinks and sports nutrition supplements contribute an additional $10 billion to the US economy every year.

In the US, the Food and Drug Administration generally regulates dietary supplements as foods and not as drugs. Because they are not regulated as drugs, people often take dietary supplements without regard for proper dosing. However, even though they are not regulated as drugs, many if not all dietary supplements have a preferred dosing range and such supplements are generally more effective and have fewer unintended side effects if they are dosed in their preferred dosage range. Accordingly, there exists a need in the art for convenient and easy to use monitoring systems and associated supplements to aid with proper dosing for dietary supplements.

BRIEF SUMMARY

Disclosed herein are methods for monitoring and adjusting a physiological state of a subject. The methods include (1) providing a subject having one or more physiological parameters defined by one or more biometrics, (2) monitoring a selected biometric analyte associated with a selected biometric to define a state of the selected biometric, (3) based on the results of the monitoring, adjusting the state of the selected biometric by administering to the subject a supplement selected to affect the state of the selected biometric.

In an embodiment, a method for monitoring and adjusting a biometric is disclosed. The method includes steps of (1) providing a subject having one or more physiological parameters defined by one or more biometrics, (2) monitoring a selected biometric analyte associated with a selected biometric to define a state of the selected biometric, (3) based on the results of the monitoring, adjusting the state of the selected biometric by administering to the subject a supplement selected to affect the state of the selected biometric.

In one embodiment, the one or more biometrics are selected from the group consisting of stress, cholesterol health, bone health, healthy blood, thyroid health, prostate health, woman's health, hydration, fertility, healthy glucose, hyperglycemia, hypoglycemia, aging, vision, sleep, immune function, energy, recovery, endurance, vitamin D, vitamin E, vitamin C, vitamin A, beta carotene, antioxidants, hormone replacement therapy, calcium, liver health, and kidney health.

In one embodiment, the selected biometric analyte is selected from the group consisting of salivary cortisol, cholesterol/apo B/LDL cholesterol/triglycerides/hdl cholesterol, 25-OH vitamin D (identify both low and high levels), osteocalcin and its derivatives, hemoglobin, TSH/free T4, PSA, FSH/estradiol, serum osmolarity (tears), urine specific gravity, estradiol/LH/progesterone/hCG (female fertility), semen analysis/resazurin/sperm count (male fertility), glucose, hemoglobin/A1c, insulin, telomere length, eye chart, salivary melatonin, salivary immunoglobulins, lactate (blood, urine, volatile organic compounds—expired air), CPK, myoglobin, vitamin D, vitamin E, vitamin C, vitamin A, beta carotene, glutamine/glutathione/conjugated dienes/ ferric reducing activity of plasma, prostaglandins, fibrinogen/sex hormone binding globulin, calcium, AST/ALT/bilirubin, BUN/creatinine, C-reactive protein, and combinations thereof.

In one embodiment, the supplement includes at least one of: i. *Cissus quadrangularis* and phosphotidylserine and one or more of valerian, Siberian ginseng, *Schisandra chinensis*, panax ginseng, *Rhodiiola rosea*, Vitamin C, hops, brazil nuts, English walnuts, fish oil, lettuce, or one or more extracts thereof; ii. red yeast rice extract, T2; iii. strontium, vitamin D3, Ca, Mg, vitamin K, and *Cissus quadrangularis*; iv. iron, folic acid, vitamin B12; v. iodine, selenium; vi. saw palmetto; vii. evening primrose; vii. phytoestrogens, black cohosh; ix. water; x. pregnancy vitamins, *lepidium meyenii, mucuna pruriens*; xi. vitamins, *lepidium meyenii, mucuna pruriens*; xii. phlorizin, glucuronidase inhibitors, glucose; xiii. acetyl carnitine, sulfurphorane; xiv. eyebright, vitamin A, blueberry; xv. light therapy, melatonin, *rhodiola rosea*; xvi. pau 'arco, siberian ginseng, schisandra *chinensis*, panax ginseng, *rhodiiola rosea*; xvii. caffeine, acetyl carnitine; xviii. glucose, acetyl coA; xix. acetyl carnitine; xx. vitamin D; xxi. vitamin E; xii. vitamin C; xxiii. vitamin A; xxiv. beta carotene; xxv. antioxidants; xxvi. estrogen and/or phytoestrogen; xxvii. calcium, vitamin D; xxviii. milk thistle; xxix. water, dandelion, ginger, juniper; or xxx. one or more of curcumin and derivatives thereof, liposomal curcumin, encapsulated curcumin, and the like, Pau 'arco, siberian ginseng, *Schisandra chinensis*, panax ginseng, *Rhodiiola rosea*, omega 3 EFA, white willow bark, green tea extract, pycneogenol, *Bogwellia serrata* resin, resveratrol, *Uncaria tomantosa, Uncria guianensia*, capsaicin, *Harpagophytm procumbens*, olive extract/olive oil, or one or more extracts thereof or pharmaceutical derivatives thereof.

In another embodiment, a method for monitoring and adjusting a biometric includes (1) providing a subject having one or more physiological parameters defined by one or more biometrics, (2) monitoring a selected biometric analyte associated with a selected biometric to define a state of the selected biometric, wherein the monitoring is performed using a monitoring apparatus that includes: an assay device configured for providing a detectable signal in response to an amount of the selected biometric analyte in a sample; a light source that is positioned to illuminate the assay apparatus with at least one wavelength of light capable of interacting with the assay apparatus and the selected biometric analyte to produce the detectable signal, wherein the light source is located on one side of the assay apparatus; a detector device that is positioned to capture the detectable signal from the assay apparatus; a holder configured to couple the assay apparatus to the detector device in proximity to the light source; a lens positioned between the detector device and the assay apparatus; and an interpretive algorithm stored in a computer readable format and electronically coupled to the detector device, wherein the interpretive algorithm is configured to convert the detectable signal to a numerical value related to the amount of the selected biometric analyte in the sample, and (3) based on the results of the monitoring, adjusting the state of the selected biometric by administering to the subject a supplement selected to affect the state of the selected biometric.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 2A and 2B illustrates a lateral flow immunoassay device according to one embodiment of the present invention;

FIGS. 3A and 3B illustrates a lateral flow immunoassay device according to another embodiment of the present invention;

FIG. 4A illustrates a plan view of a diagnostic test system that includes a digital camera device and a testing apparatus configured to couple the lateral-flow chromatographic immunoassay cassette to the digital camera device;

FIG. 4B illustrates a side view of the diagnostic test system of FIG. 4A;

DETAILED DESCRIPTION

Figure 1:
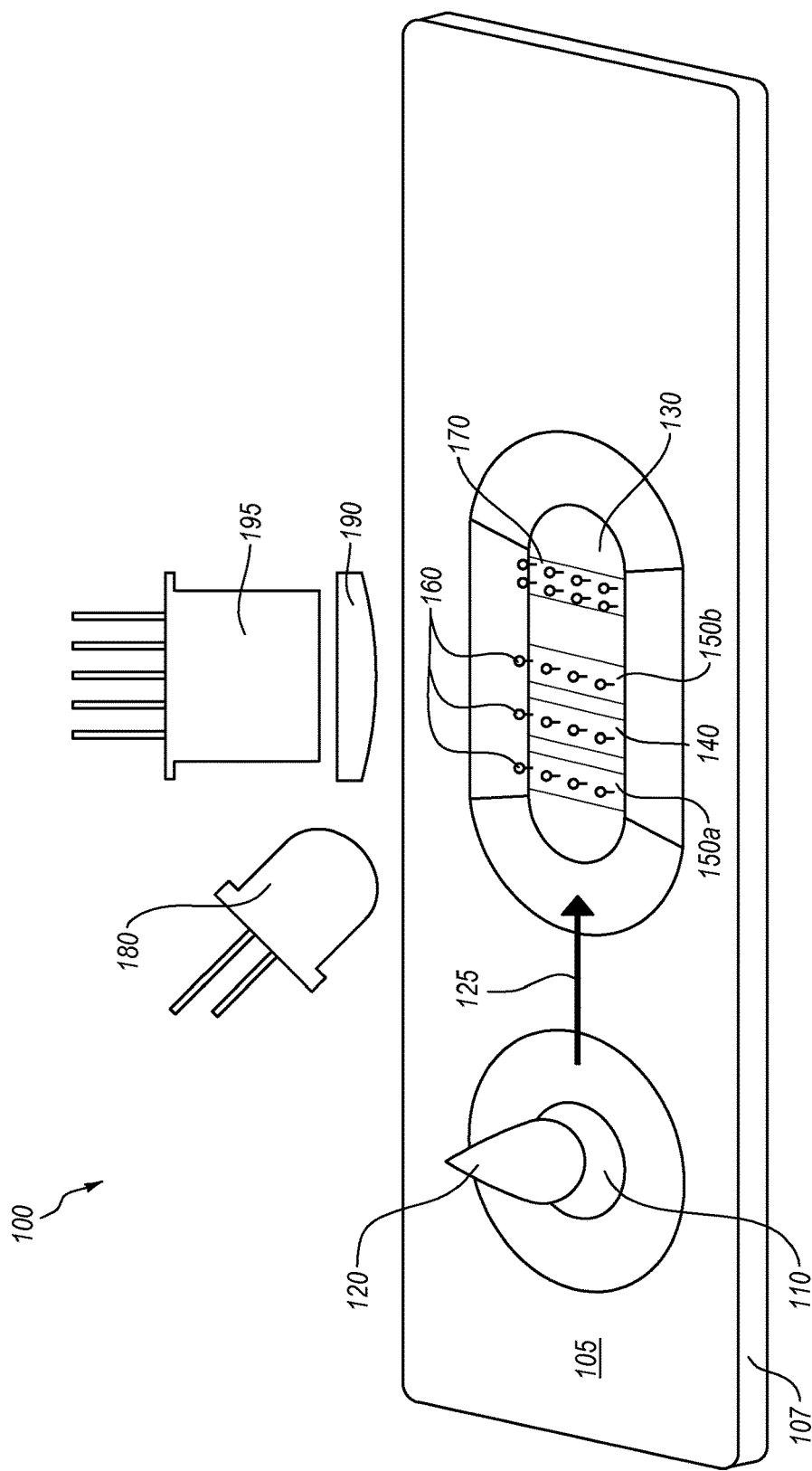
FIG. 1 illustrates a perspective view of a diagnostic test system, according to one embodiment of the present disclosure.

Disclosed herein are methods for assessing and adjusting a physiological state of a subject. The methods include (1) providing a subject having one or more physiological parameters defined by one or more biometrics, (2) monitoring a selected biometric analyte associated with a selected biometric to define a state of the selected biometric, (3) based on the results of the monitoring, adjusting the state of the selected biometric by administering to the subject a supplement selected to affect the state of the selected biometric. In one embodiment, the subject may be a human or an animal, such as, but not limited to, a cow, a sheep, a pig, a horse, a chicken, a dog, a cat, and the like.

In the methods described herein, the supplement formulation may be administered in a manner selected from the group consisting of: (1) oral administration, (2) intranasal administration, (3) transmucosal administration, (4) parenteral injection, (5) implant for sustained release, (6) transdermal patch, and combinations thereof. The typical route of administration for supplements is oral.

Additionally, the supplement formulation described herein can be incorporated into a number of food and/or beverage compositions to form a fortified food or beverage compositions. Suitable examples of foods and/or beverages include, but are not limited to, processed meat products, processed fish products, gels such as energy gels, jams, pastes, nutrition bars, bakery products, creams, sauces, dairy products, confections, syrups, pet foods, water-based beverages, dairy-based beverages, complex carbohydrates, fats, proteins, prepared foods and beverages, supplement capsules, pills, tablets, or powders, and combinations thereof.

Preferably, the fortified food or beverage compositions described herein includes about 0.01 wt % to about 99.9 wt % of the compound of the supplement formulation, or, more preferably, about 0.1 wt % to about 60 wt % of the supplement formulation, or, most preferably, about 1 wt % to about 50 wt % of the supplement formulation.

The methods disclosed herein may allow assessment and identification of a need for one or more supplements that may enhance the physiological well being of a subject. Likewise and in addition, the methods disclosed herein allow for assessment of the dosing of supplements that the subject is already taking. Such methods may be configured for allowing the subject to assess need(s) and customize dosing according to monitoring of one or biometric parameters discussed herein. A listing of biometrics, personal biometric analytes, and associated supplements are shown below in Table 1.

TABLE 1

| Biometric | Personal Biometric Analyte | Dietary Supplement |
|---|---|---|
| Stress | Salivary cortisol | *Cissus quadrangularis,* Phosphotidylserine, valerian, Siberian ginseng, *Schisandra chinensis, Panax ginseng, Rhodiiola rosea,* Vitamin C |

TABLE 1-continued

| Biometric | Personal Biometric Analyte | Dietary Supplement |
|---|---|---|
| Cholesterol health | Cholesterol/apo B<br>LDL cholesterol and its derivatives (e.g., oxidized LDL), triglycerides, hdl cholesterol | red yeast rice extract, T2 |
| Bone health | 25-OH vitamin D (identify both low and high levels), osteocalcin and its derivatives | Strontium, vitamin D3, Ca, Mg, vitamin K, *Cissus quadrangularis*, vitamin D |
| Healthy blood | Hemoglobin | Fe, folic acid, vitamin $B_{12}$ |
| Thyroid health | TSH, free T4 | Iodine, selenium |
| Prostate health | PSA | Saw palmetto |
| Woman's health | FSH, estradiol, | Evening primrose, phytoestrogens, black cohosh |
| Hydration | Serum osmolarity (tears)<br>Urine specific gravity | water |
| Fertility | Female: estradiol, LH, progesterone, hCG<br>Male: semen analysis (resazurin, sperm count) | Pregnancy vitamins, *Lepidium meyenii*, *Mucuna pruriens* vitamins, *Lepidium meyenii*, *Mucuna pruriens* |
| Healthy glucose (hyper and hypoglycemia) | Glucose, hemoglobin A1c insulin | Phlorizin, (glucuronidase inhibitors), glucose |
| aging | telomere length (point of care) | acetyl carnitine, sulfurphorane |
| vision | eye chart | eyebright, vitamin A, blueberry |
| Sleep | Salivary melatonin | Light, melatonin, *Rhodiola rosea* |
| Immune function | Salivary immunoglobulins | Pau 'arco, Siberian *ginseng*, *Schisandra chinensis*, *Panax ginseng*, *Rhodiiola rosea* |
| Immune function | C-reactive protein | Curcumin and derivatives thereof, liposomal curcumin, encapsulated curcumin and optionally one or more of, Pau 'arco, Siberian *ginseng*, *Schisandra chinensis*, *Panax ginseng*, *Rhodiiola rosea*, omega 3 EFA, white willow bark, green tea extract, pycneogenol, *Bogwellia serrata* resin, resveratrol, *Uncaria tomantosa*, *Uncria guianensia*, capsaicin, Harpagophytm procumbens, olive extract/olive oil |
| sports | | |
| energy | Heart rate, hemoglobin | caffeine, acetyl carnitine |
| recovery | lactate (blood, urine, volatile organic compounds—expired air) | glucose, acetyl coA |
| endurance | CPK, myoglobin | actyl carnitine |
| more is not better | | |
| vitamin D | vitamin D | vitamin D |
| vitamin E | vitamin E | vitamin E |
| vitamin C | vitamin C | vitamin C |
| vitamin A | vitamin A | vitamin A |
| beta carotene | beta carotene | beta carotene |
| antioxidants | glutamine/glutathione, conjugated dienes, ferric reducing activity of plasma, prostaglandins and their derivatives | antioxidants |
| hormone replacement therapy | fibrinogen, sex hormone binding globulin | estrogens |
| calcium | calcium | Calcium, vitamin D |
| Liver health | AST, ALT, bilirubin | Milk thistle |
| Kidney health | BUN, creatinine | Water, dandelion, ginger, juniper |

Of the personal biometric analytes listed in Table 1, assessment of male fertility (i.e., sperm analysis), visual acuity, and telomere length can each be readily tested in a doctor's office or in a medical testing laboratory. Point of care diagnostic tests that can be performed by nonmedical personnel (e.g., at home) could also be developed to provide this information. Additionally, each of salivary cortisol, cholesterol/apo B, 25-OH vitamin D (identify both low and high levels), osteocalcin, hemoglobin, TSH/free T4, PSA, FSH/estradiol, serum osmolarity (tears), urine specific gravity, estradiol/LH/progesterone/hCG (female fertility), glucose, hemoglobin A1c, insulin, salivary melatonin, salivary immunoglobulins, lactate (blood, urine, volatile organic compounds—expired air), CPK, myoglobin, vitamin D, vitamin E, vitamin C, vitamin A, beta carotene, glutamine/glutathione/conjugated dienes/ferric reducing activity of plasma, fibrinogen/sex hormone binding globulin, and calcium are amenable to chemical and/or immunoassay testing that can be performed in the home or at the point of care with rapid, handheld testing devices.

In a specific but non-limiting embodiment, the methods may further include monitoring salivary cortisol in the subject and administering to the subject an amount of a supplement formulation effective for reducing cortisol levels. Elevated cortisol is associated with prolonged stress and many of the negative consequences of stress are tied to the effects of cortisol. As a result, lowering cortisol levels can lessen the consequences associated with prolonged stress. In one embodiment, salivary cortisol levels can be measured by assaying a saliva sample with a lateral flow immunoassay cassette like those shown in FIGS. 1-3B.

In one embodiment, salivary cortisol can be assayed by applying a saliva sample to the test sample pad and a calibration sample to the calibration sample pad and running the samples out on the lateral flow device. The results of such a lateral flow assay can be read and quantified with an electro-optical device that is configured for reading such an assay. An example of an electro-optical device suitable for use in the method disclosed herein, without limitation, is described herein below.

In an embodiment, the supplement formulation effective for reducing cortisol levels includes Cissus quadrangularis and phosphotidylserine or pharmaceutical derivatives thereof. The supplement formulation includes a daily dosage of between about 10 mg and about 15,000 mg of Cissus quadrangularis (e.g., about 500 mg to about 12,000 mg or 50 mg to about 500 mg) and a daily dosage of between about 10 mg and about 1000 mg of phosphotidylserine (e.g., about 20 mg to about 250 mg).

In one embodiment, the Cissus quadrangularis in the daily dosage includes at least one of (i) a plant part of Cissus quadrangularis (e.g., dried Cissus quadrangularis) or (ii) a chemical extract (e.g., an ethanolic extract) of a plant part of Cissus quadrangularis.

Cissus quadrangularis is a perennial plant of the grape family. It is commonly known as veldt grape or devil's backbone. Cissus quadrangularis has been found to contain a rich source of carotenoids, triterpenoids, including α- and β-amyrins, β-sitosterol, ketosteroid, phenols, tannins, carotene, and vitamin C. Cissus quadrangularis is a cortisol antagonist—i.e., Cissus quadrangularis interferes with the physiological action of cortisol, which lessens the effects associated with elevated cortisol levels. In one assay, a Cissus quadrangularis extract has been found to be about 4% as potent as mifepristone as a glucocorticoid antagonist. Mifepristone is a potent and well-known glucocorticoid antagonist. In another assay, a powder extract of Cissus quadrangularis was found, in vitro, to have glucocorticoid receptor antagonist activity and no agonist activity or toxicity.

Phosphotidylserine is a phospholipid component, usually kept on the inner-leaflet (the cytosolic side) of cell membranes by an enzyme called flippase. Administration of phosphotidylserine is associated with improved memory and cognition. In sports nutrition studies, phosphotidylserine has been demonstrated to speed up recovery, prevent muscle soreness, improve well-being, and might possess ergogenic properties in athletes involved in cycling, weight training and endurance running. In the body, phosphotidylserine is believed to block the release of cortisol.

It is believed that Cissus quadrangularis and phosphotidylserine may act synergistically in the present supplement formulation. That is, while each may target cortisol individually, together they both antagonize and block the release of cortisol. This is believed to magnify the effect of either alone. As such, it may be possible to reduce the dosage of Cissus quadrangularis and phosphotidylserine when administered together compared to the dosages that would be required with either drug administered alone. Moreover, it is believed that Cissus quadrangularis and phosphotidylserine are capable of working together to lower cortisol levels and/or combat the effects of stress in a way that is unique compared to either alone.

In an additional embodiment, the supplement formulation is combined with one or more of pharmacological compounds that block the release of ACTH (e.g., CRH antagonists) or pharmacologic compounds that block glucocorticoid action (e.g., mifepristone). Additional discussion of pharmacologic compounds that block glucocorticoid action (i.e., glucocorticoid antagonists) can be found in U.S. patent application Ser. No. 14/105,927 filed 13 Dec. 2013, the entirety of which is incorporated herein by reference.

In one embodiment, the supplement formulation may further include a daily dosage of between about 10 mg and about 10,000 mg of one or more of valerian, hops, Brazil nuts, English walnuts, fish oil, lettuces, or one or more extracts thereof. Additionally, the supplement may further include a daily dosage of between about 10 mg and about 10,000 mg of at least one of vitamin C or l-tyrosine.

Hops, Brazil nuts, English walnuts, fish oil, and lettuces have a general calming effect. And while it is not known, one or more of them may block the release of cortisol or may act as a cortisol antagonist.

For example, Brazil nuts, English walnuts may have a general calming property due to the fact that they are naturally high in bromine Bromide compounds, especially potassium bromide, are known to have a sedative effect and bromides were frequently used as sedatives in the 19th and early 20th century.

In another example, lettuces may have a general calming effect due to the presence of an alkaloid called lactucarium that is present in lettuces. Lactucarium is known as lettuce opium because of its sedative and analgesic properties. Lactucarium is the milky fluid secreted by several species of lettuce, such as Lactuca virosa, Lactuca canadensis, Lactuca serriola, and even culinary varieties like from Lactuca sativa. In one embodiment, the supplement may include an extract of lettuce that includes lactucarium.

In another example, studies have shown that ingestion of 1 gram of vitamin C for 7 days blunts the cortisol rise in response to lipopolysaccharide administration. Likewise, administration of 9 grams of tyrosine improves cognitive function following experimentally induced hypothermia. Likewise, valerian is known to have sedative, which may be linked to cortisol.

In an embodiment, a method for reducing stress, enhancing mood, and/or treating a physical or psychological condition caused by stress in a mammal (e.g., a human) is disclosed. The method includes (1) administering to the mammal an amount of a supplement formulation that includes Cissus quadrangularis and phosphotidylserine or pharmaceutical derivatives thereof, and (2) achieving an effect of reducing stress, enhancing mood, and/or treating a physical or psychological condition caused by stress in the mammal. In one embodiment, the amount of the supplement formulation includes a daily dosage of between about 10 mg and about 15,000 mg of Cissus quadrangularis including an extract thereof and a daily dosage of between about 10 mg and about 1000 mg of phosphotidylserine. Suitable examples of mammals include, but are not limited to, humans, non-human primates, dogs, cats, horses, mice, rats, sheep, cattle, and the like.

In yet another embodiment, a method for reducing a cortisol level in a subject is disclosed. The method includes (1) providing a subject having an elevated cortisol level, (2) administering to the subject an amount of a supplement formulation that includes *Cissus quadrangularis* and phosphotidylserine or pharmaceutical and natural product derivatives thereof, and (3) achieving an effect of reducing the cortisol level in the subject in response to administering the supplement formulation.

The subject having an elevated cortisol level may be identified by testing one or more body fluids of the subject to determine if cortisol levels are elevated (as compared to a baseline control). For example, cortisol level can be determined by assaying the blood or the saliva or the urine of the subject. In another, a subject having elevated cortisol may be identified by interviewing the subject to see if the subject suffers from stress, and/or treating a physical or psychological condition caused by stress. In addition, individuals may self-identify themselves as being under stress or as suffering from stress.

In one embodiment, reducing the cortisol level in the subject produces an effect of enhancing mood and/or treating a physical or psychological condition caused by stress in the subject. Likewise, reducing the cortisol level in the subject will generally promote weight loss, help normalize elevations in blood glucose, decrease bruisability, decrease muscle weakness, blunt mood swings, and the like.

In the methods described above, the *Cissus quadrangularis* in the supplement formulation includes at least one of (i) a plant part of *Cissus quadrangularis* or (ii) a chemical extract of a plant part of *Cissus quadrangularis*.

In the methods described above, the supplement formulation further includes a daily dosage of between about 10 mg and about 10,000 mg of one or more of hops, Brazil nuts, English walnuts, fish oil, lettuce, or one or more extracts thereof. In one embodiment, an extract of lettuce includes lactucarium.

In one embodiment the supplement formulation further comprises a daily dosage of between about 10 mg and about 10,000 mg of at least one of vitamin C or l-tyrosine.

In one embodiment, the method further includes monitoring cortisol levels (e.g., salivary cortisol) in the subject, wherein elevated cortisol is associated with stress; administering to the subject an amount of a supplement formulation that includes a blend of *Cissus quadrangularis* and phosphotidylserine and one or more of valerian, Siberian ginseng, *Schisandra chinensis*, panax ginseng, *Rhodiiola rosea*, Vitamin C, hops, brazil nuts, English walnuts, fish oil, and lettuce, or one or more extracts thereof or pharmaceutical derivatives thereof.

Depending on the results of the measuring—i.e., the amount of cortisol measured—such a supplement may be administered at a dosage comprising a daily dosage of between about 10 mg and about 15,000 mg of *Cissus quadrangularis* and a daily dosage of between about 10 mg and about 1000 mg of phosphotidylserine, and a daily dosage between about 10 mg and about 10,000 mg of one or more of Siberian ginseng, *Schisandra chinensis*, panax ginseng, *Rhodiiola rosea*, Vitamin C, hops, Brazil nuts, English walnuts, fish oil, and lettuces.

In one embodiment, such a dosage may have an effect of reducing stress, enhancing mood, and/or treating a physical or psychological condition caused by stress in the subject. In another embodiment, such a dosage may further have an effect of achieving an effect of lowering salivary cortisol in the subject.

Additional discussion of such a supplement, its ingredients, and dosing may be found in U.S. Prov. App. Ser. No. 61/740,979 entitled "A DIETARY SUPPLEMENT FORMULATION FOR COMBATTING STRESS AND METHODS FOR COMBATTING STRESS" filed 21 Dec. 2012, the entirety of which is incorporated herein by reference.

According to the present disclosure, additional biometrics, such as, but not limited to, cholesterol health, bone health, healthy blood, thyroid health, prostate health, woman's health, hydration, fertility, healthy glucose, hyperglycemia, hypoglycemia, aging, vision, sleep, immune function, energy, recovery, endurance, vitamin D, vitamin E, vitamin C, vitamin A, beta carotene, antioxidants, hormone replacement therapy, calcium, liver health, kidney health, nutrition, and combinations can be monitored/assessed with selected associated biometric analytes. The results of such assessment can be used to select associated supplements for ingestion by the subject and/or adjustment of the dosing of supplements already being taken by the subject in a manner similar to the stress/salivary cortisol example discussed above.

In another specific, non-limiting example of the methods described herein, the methods may further include monitoring levels in the subject of C-reactive protein (CRP) in one or more bodily fluids, such as, but not limited to, blood (e.g., serum), saliva, lymph fluid, and urine. CRP shows a marked increase in response to a variety of acute and chronic stimuli including infection, burns, surgery, major trauma and other inflammatory conditions; CRP concentration may be increased by as much as 100-fold or more in response to such acute and chronic stimuli. In saliva CRP may be a marker of oral health, e.g. whether periodontal, gingival, or dental disease is present.

CRP is synthesized in the liver as well as other sites, such as the oral mucosa. It is a protein of molecular weight 1.15 kD, composed of 5 identical subunits arranged as a cyclic pentameter. CRP is a normal constituent of human serum, found in all age groups with no difference in the mean serum concentrations between men and women. CRP levels are higher in late pregnancy but not elevated in women on the oral contraceptive pill. The normal CRP concentration in serum concentration is generally regarded as <10 mg/L in adults, although a few healthy people have a slightly higher value.

Following an acute stimulus the plasma concentration of CRP rises within 6 hrs, and may double every 8 hrs thereafter, reaching a peak at around 50 hrs. Similarly, on cessation of the stimulus, the plasma CRP concentration declines rapidly in an exponential manner, the half-life of the molecule in the circulation being 5-7 hrs.

The major functions of CRP are not known. However, it has been reported to interact with the immune system and inflammatory pathways. CRP is known to bind to bacterial cell walls and to activate the classical complement pathway, hence it may act as a component of non-adaptive immunity amplifying the response. In vitro, CRP has been shown to bind to neutrophils without activating them. CRP does not mediate leukocyte aggregation.

It is believed that CRP levels can be used to monitor immune function and the state of various challenges to the immune system as a result of various acute and chronic stimuli. In one embodiment, levels of CRP can be measured by assaying a bodily fluid (e.g., serum, saliva, or urine) with a lateral flow immunoassay cassette like those shown in FIGS. 1 and 2.

In one embodiment, salivary CRP can be assayed by applying a saliva sample to the test sample pad and a calibration sample to the calibration sample pad and running the samples out on the lateral flow device. Serum and urine levels of CRP can be assayed similarly. The results of such a lateral flow assay can be read and quantified with an electro-optical device that is configured for reading such an assay.

In one embodiment, the method further includes administering to the subject an amount of a supplement formulation that includes one or more of curcumin and derivatives thereof, liposomal curcumin, encapsulated curcumin, and the like, and optionally one or more of Pau 'arco, siberian ginseng, *Schisandra chinensis*, panax ginseng, *Rhodiiola rosea*, omega 3 EFA, white willow bark, green tea extract, pycneogenol, *Bogwellia serrata* resin, resveratrol, *Uncaria tomantosa, Uncria guianensia*, capsaicin, *Harpagophytm procumbens*, olive extract/olive oil, or one or more extracts thereof or pharmaceutical derivatives thereof.

Curcumin is the principal curcuminoid of the spice turmeric. Turmeric's other two curcuminoids are desmethoxycurcumin and bis-desmethoxycurcumin. The curcuminoids are natural phenols that are responsible for the yellow color of turmeric. Laboratory research shows that curcumin is capable of interacting with molecular targets involved in inflammation. In vitro, curcumin modulates the inflammatory response by down-regulating the activity of cyclooxygenase-2, lipoxygenase, and inducible nitric oxide synthase enzymes; and inhibits several other enzymes involved in inflammation mechanisms. However, dietary curcumin has been shown to exhibit poor bioavailability (i.e., low levels in plasma and tissues). Potential factors that limit the bioavailability of curcumin include poor absorption, rapid metabolism, and rapid systemic elimination. One way that the bioavailability of curcumin may be increased is to incorporate into liposomes and/or other encapsulating techniques known in the art. Likewise, the bioavailability of curcumin may be increases by derivatizing the cucumin molecule to increase its solubility in aqueous fluids. Pau 'arco may have immune enhancing properties. Siberian ginseng, *Schisandra chinensis*, panax ginseng, *Rhodiiola rosea* are general calming agents and may alter or improve immune function. Omega 3 EFA, white willow bark, green tea extract, pycneogenol, *Bogwellia serrata* resin, resveratrol, *Uncaria tomantosa, Uncria guianensia*, capsaicin, *Harpagophytm procumbens*, and olive extract/olive oil may have immune enhancing properties and are believed to alter or improve immune function Depending on the results of the measuring—i.e., the amount of CRP measured—such a supplement may be administered at a dosage comprising a daily dosage of between about 10 mg and about 10,000 mg of curcumin and derivatives thereof, liposomal curcumin, encapsulated curcumin Depending on the results of the measuring, such a supplement may also include a daily dosage between about 10 mg and about 10,000 mg of one or more of Siberian ginseng, *Schisandra chinensis*, panax ginseng, and *Rhodiiola rosea*. Depending on the results of the measuring, such a supplement may also include a daily dosage between about 10 mg and about 10,000 mg of one or more of omega 3 EFA, white willow bark, green tea extract, pycneogenol, *Bogwellia serrata* resin, resveratrol, *Uncaria tomantosa, Uncria guianensia*, capsaicin, *Harpagophytm procumbens*, and olive extract/olive oil.

In one embodiment, such a dosage may have an effect of improving immune function, reducing the impacts of the inflammatory response, and/or treating a physical condition caused by various acute and chronic stimuli (e.g., bacterial or viral infection, cancer, etc.). In another embodiment, such a dosage may further have an effect of achieving an effect of lowering CRP levels in the subject.

Diagnostic Test Systems

In embodiment, a diagnostic test system, as described herein, can be used in the methods described herein to assay one or more of the personal biometric analytes. For example, the diagnostic test system can be used for assaying cortisol and/or CRP as in the methods described in detail above. The system includes a lateral-flow chromatographic assay cassette and a testing device that includes data collection and data analysis capabilities. The testing device is configured to interface with and analyze output of the lateral-flow chromatographic assay cassette.

Referring to FIG. 1, perspective view of a diagnostic test system 100 is illustrated. The diagnostic test system 100 includes a lateral-flow chromatographic assay cassette 105 and means for collecting assay data from the lateral-flow chromatographic assay cassette 105.

The lateral-flow chromatographic assay cassette 105 includes a plastic housing 107 containing a test strip, which is generally a plastic strip laminated with porous material that permits lateral flow of liquid. The illustrated lateral-flow chromatographic immunoassay cassette 105 includes a sample application zone 110 and an analysis zone 130.

When a sample 120 is applied to the lateral-flow chromatographic immunoassay cassette 105 at the sample application zone 110, the sample 120 diffuses through the strip in flow direction 125 toward the analysis zone 130. In the embodiment illustrated in FIG. 1, the analysis zone 130 includes a test line 140 that includes at least one capture ligand selected for capturing at least one analyte of interest in the sample 120. The analysis zone 130 further includes at least first and second calibration standard lines 150a and 150b. Additionally, the analysis zone may include a positive control line 170 that may be configured to provide an indication regarding whether or not sample has diffused though the strip and whether or not the assay is functioning. For example, the positive control line 170 may include a water soluble dye that is positioned and configures to indicate that the sample has flowed the length of/traversed the test strip.

The analyte(s) of interest, the first and second calibration standards, and the positive control can be detected on their various target lines, 140, 150a, 150b and 170, respectively, with various reporters. The reporters 160 for each of the various target lines, 140, 150a, 150b and 170, may be the same or different. Examples of suitable reporters include, but are not limited to, visible and fluorescent dyes, latex beads, enzymes, gold nanoparticles, silver nanoparticles, titanium nanoparticles, europium fluorophores, quantum dots, Raman spectroscopy, and the like. Quantum dots are nano-scale materials that can produce excited emission at particular wavelengths depending on their size and shape. Quantum dots can be used in immunoassays where dyes have traditionally been used. However, quantum dots are generally superior to traditional organic dyes on several counts: quantum dots are typically much brighter that organic dyes (owing to their high extinction coefficients combined with a comparable quantum yield to fluorescent dyes) as well as their stability (i.e., much less photobleaching). For example, it has been estimated that quantum dots are 20 times brighter and 100 times more stable than traditional fluorescent reporters.

Emission (i.e., a detectable signal) from the various reporters can be excited by a number of sources. In the illustrated embodiment, an LED light source 180 is used illuminate the analysis zone 130 of the lateral flow assay cassette 105. Illumination by the light source 180 may produce a detectable signal that includes at least one of emission (e.g., fluorescence), color, reflectance, diffuse scattering (i.e., scattering and absorbance), elastic light scattering, chemiluminescence, chemifluorescence, transmission, plasmon surface resonance, or absorbance from the reporters. A lens 190 (e.g., a collimating lens) and a detector 195 (e.g., a CCD or CMOS camera) are used to collect data from the reporters and the first and second calibration standards.

When the sample 120 is applied to the diffusion strip of the lateral-flow chromatographic assay cassette 105, the liquid in the sample carries the analyte of interest through the diffusion strip in flow direction 125 into the analysis zone 130 where it can be captured by the capture ligand line 140. The first and second calibration standard lines 150*a* and 150*b* are selected to provide a detectable signal that correlate to non-zero concentration values of the analyte of interest. For example, the first and second calibration standard lines 150*a* and 150*b* may include an amount of the analyte of interest or another material pre-bound to the diffusion strip of the lateral-flow chromatographic assay cassette 105. The reporter 160 may be a diffusible material that can bind to the capture ligand line 150 and the first and second calibration standards 150*a* and 150*b* in an amount proportional to the amount of bound ligand is present in each line. In response to illumination by the light source, the reporter 160 bound to each of lines 140, 150*a*, and 150*b* provides a signal that can be used to calculate a calibration curves and, in turn, determine the concentration of the analyte of interest in the sample 120. A more detailed discussion of methods for deriving analyte concentration from the data of the first and second calibration standards 150*a* and 150*b* and the capture line 140 is discussed in greater detail elsewhere herein.

In one type of lateral-flow chromatographic immunoassay cassette, the test strip is divided into four domains, which can be made of only one kind of material or several kinds of material (e.g., up to four different kinds of materials). The first domain is for sample addition. It functions to remove viscous and particulate materials in the sample and also to condition the sample solution for the reactions in the following domains. The second domain is a mobile-phase with a color conjugate. In one embodiment, the color conjugate may be made from conjugation between a visible color marker (e.g., colored beads, colloidal gold, fluorescent dyes, etc.) and a detection antibody. The detection antibody can bind a specific antigen in the sample (e.g., an analyte of interest or a positive control substance) and forms an antigen-color conjugate complex. The third domain of the lateral-flow chromatographic immunoassay cassette is a solid-phase with immobilized capture antibody. The capture antibody can bind the antigen of the antigen-color conjugate complex and forms capture antibody-antigen-color conjugate complex sandwich. The fourth domain is for solution absorption. It draws sample solution towards it continuously.

During the testing, sample added to the first domain flows to the second domain. If the antigen is present in the sample, it will bind the color conjugate to form antigen-color conjugate complex. This complex then migrates to the third domain to bind the capture antibody and forms the capture antibody-antigen-color conjugate complex sandwich. Since the capture antibody is immobilized in the third domain, the sandwich shows as a visible color signal or a fluorescent signal, depending on the dye type, on the site of the capture antibody. If there is no antigen in the sample, no sandwich can be formed and hence no visible color signal can be seen in the third domain. This is a so-called non-competitive immunoassay or a sandwich assay where the amount of signal is directly proportional to the concentration of the analyte of interest in the sample.

Lateral-flow chromatographic immunoassay cassettes can also be adapted for competitive immunoassays. In a competitive immunoassay, the analyte of interest in the unknown sample competes for binding to an antibody with a labeled analyte. In a competitive assay, the labeled analyte is able to provide a known signal. In the assay, the amount of labeled analyte bound to the antibody is measured and any reduction in the known signal is attributed to the presence of the analyte in the sample. That is, in this method, the response will be inversely related to the concentration of analyte in the unknown. This is because the greater the response, the less antigen in the unknown was available to compete with the labeled antigen.

Lateral-flow chromatographic immunoassay cassettes may be adapted for assaying a number of different analyte types. For example, immunoassay cassettes have been adapted or may in the future be adapted for blood glucose testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, complete blood count ("CBC"), hemoglobin diagnostics, infectious disease testing (e.g., a multi-analyte rapid diagnostic test for detecting malaria infection), cholesterol screening, hormone testing, cardiac pulmonary, gastroenterology, urology, renal, dermatology, neurology, pediatrics, surgical, public health, and veterinary and plant pathology testing, genomic testing including the identification of DNA, RNA, and histones, combinations thereof, and the like. Likewise, immunoassay cassettes have been adapted or may in the future be adapted for assaying one or more of salivary cortisol, cholesterol/apo B/LDL cholesterol/triglycerides/hdl cholesterol, 25-OH vitamin D (identify both low and high levels), osteocalcin and its derivatives, hemoglobin, TSH/free T4, PSA, FSH/estradiol, serum osmolarity (tears), urine specific gravity, estradiol/LH/progesterone/hCG (female fertility), semen analysis/resazurin/sperm count (male fertility), glucose, hemoglobin/A1c, insulin, telomere length, eye chart, salivary melatonin, salivary immunoglobulins, lactate (blood, urine, volatile organic compounds—expired air), CPK, myoglobin, vitamin D, vitamin E, vitamin C, vitamin A, beta carotene, glutamine/glutathione/conjugated dienes/ferric reducing activity of plasma, prostaglandins, fibrinogen/sex hormone binding globulin, calcium, AST/ALT/bilirubin, BUN/creatinine, C-reactive protein, and combinations thereof.

In addition to the foregoing, another embodiment of a lateral flow immunoassay cassette is described. Examples of such lateral flow immunoassay cassettes are shown at 200 in FIGS. 2A and 2B and at 300 in FIGS. 3A and 3B. In the lateral flow immunoassay cassettes 200 and 300, a test sample (i.e., a sample containing an unknown concentration of an analyte of interest) may be run in parallel with a calibration standard (i.e., a sample containing a known concentration of the analyte of interest). The response to the known concentration of the analyte of interest in the calibration standard on the lateral flow immunoassay device may be used to generate a calibration curve that can be used to quantify the amount of the analyte of interest in the test sample.

Such an arrangement may provide superior results. For example, the test and calibrations strips of such cassettes may be manufactured side-by-side under substantially equal temperature and humidity conditions. As a result, it is generally the case that the test and calibrations strips each have the same amount on antibody immobilized thereon and that the antibody on each will react substantially the same. Also, because the test and calibration assays are run in parallel, the test and calibration results are generally unaffected by factors like temperature and humidity. This is generally not the case if the test and calibration assays are run at separate times on strips that may have been manufactured at different times. Likewise, because the test and calibration assays are run in parallel, the cassettes and a reader device, if used, are calibrated for each assay run on each cassette, which is believed to provide more reliable quantitative results.

The lateral flow immunoassay cassette 200 illustrated in FIGS. 2A and 2B includes a base 214 that includes a test strip 201a and a calibration strip 201b. The test strip 201a includes a sample application zone 202a with a sample collection pad 216a, a conjugate pad 204a, a test assay strip 206a (e.g., a nitrocellulose ("NC") membrane), and an absorbent pad 212. Likewise, the calibration strip 201b includes a sample application zone 202b with a sample collection pad 216b, a conjugate pad 204b, a calibration strip 206b, and the absorbent pad 212. Each of the test assay strip 206a and the calibration strip 206b include at least one capture binding moiety 208a and 208b (e.g., an antibody, a nucleic acid, or the like) that can specifically interact with and capture the analyte of interest for detection. In one embodiment, the sample pad 212 may include flow indicator lines 210a and 210b (e.g., a water soluble dye) that indicate whether or not sample has successfully diffused through the test strip 201a and the calibration strip 201b.

In the illustrated embodiment, the test 201a and calibration strips 201b are run in opposite directions (i.e., both the test sample and calibration standard flow toward absorbent pad at the center of the cassette). In other embodiments, the test and calibration strips may be arranged such that the test sample and calibration standard flow parallel to one another. Such an embodiment may, for example, include a divider arranged between the test assay strip and the calibration assay strip.

The lateral flow immunoassay cassette 300 illustrated in FIGS. 3A and 3B is similar to the cassette 200 of FIGS. 2A and 2B. The lateral flow immunoassay cassette 300 includes a base 314 that includes a test strip 301a and a calibration strip 301b. The test strip 301a includes a sample application zone 302a with a sample collection pad 316, a conjugate pad 304a, a test assay strip 306a (e.g., a nitrocellulose ("NC") membrane), and an absorbent pad 312. In addition, the test strip 301a includes a sachet 320 (e.g., a blister pack) of buffer that can be used to chase (i.e., wash) a test sample through the conjugate pad 304a and the assay strip 306a toward the absorbent pad 312.

In contrast to the cassette 200 of FIGS. 2A and 2B, the cassette 300 omits a calibration standard application zone and instead includes a standard solution sachet 318 that contains a known volume of a solution that contains a known amount of at least one analyte of interest. When the a standard solution sachet 318 is pierced at the time of use, the solution wicks through the conjugate pad 304b and the calibration strip 306b toward the absorbent pad 312. Each of the test assay strip 306a and the calibration strip 306b include at least one capture binding moiety 308a and 308b (e.g., an antibody, a nucleic acid, or the like) that can specifically interact with and capture the analyte of interest for detection. The characteristics of the standard solution sachet 318 can be used to test for quantitative delivery of the calibration standard onto the calibration strip 306b and to test the response of the capture binding moiety 308b to the analyte of interest. In one embodiment, the sample pad 312 may include flow indicator lines 310a and 310b (e.g., a water soluble dye) that indicate whether or not sample has successfully diffused through the test strip 301a and the calibration strip 301b.

In one embodiment, the sample pad 216a, 216b, or 316 may be configured to absorb and dispense a predetermined amount of a fluid from the fluid that is applied thereto. That is, the sample pad 216a, 216b, or 316 may be fabricated from an absorbent-type material that may saturated with fluid and then when, for example, the sample pad 216a, 216b, or 316 is compresses or squeezed, the sample pad 216a, 216b, or 316 can dispense a predetermined amount of a fluid therefrom. In one embodiment, the sample pad 216a, 216b, or 316 may be made of cellulose, glass fiber or other material where the fluid sample is applied to the lateral flow device and, if necessary modifies it to improve the results of the assay. This might be by modifying pH, filtering out solid components, separating whole blood constituents, adsorbing out unwanted antibodies or some other test specific variable.

For some applications, the sample pad 216a, 216b, or 316 may be pretreated by dipping it into a specific buffer containing a mix of a solution comprised of soluble proteins, surfactants/detergents, and other polymers. These may allow for a steady flow and prevent nonspecific binding of sample components to the pad 216a, 216b, or 316.

In some embodiments, the sample may be added to the sample pad 216a, 216b, or 316 by collecting a liquid sample (e.g., blood, urine, or saliva) and adding a selected volume of the sample to the sample pad. In other embodiment, the sample may be added to the sample pad 216a, 216b, or 316 by soaking the pad with a fluid sample. For example, the sample pad 216a, 216b, or 316 may be soaked with saliva by inserting the sample collection pad 216a, 216b, or 316 end of the device 200 or 300 into the mouth to collect a saliva sample.

In one embodiment, the sample pad may be configured to absorb and dispense a predetermined amount of a fluid from the fluid that is applied thereto. That is, the sample pad may be fabricated from an absorbent-type material that may saturated with fluid and then when, for example, the sample pad is compressed or squeezed, the sample pad can dispense a predetermined amount of a fluid therefrom. In one embodiment, the sample pad is made of cellulose, glass fiber or other material where the fluid sample is applied to the lateral flow device and, if necessary modifies it to improve the results of the assay. This might be by modifying pH, filtering out solid components, separating whole blood constituents, adsorbing out unwanted antibodies or some other test specific variable.

For some applications, the sample pad may be pretreated by dipping it into a specific buffer containing a mix of a solution comprised of soluble proteins, surfactants/detergents, and other polymers. These allow for a steady flow and prevent nonspecific binding of sample components to the pad.

In one embodiment, the conjugate pad 204a, 204b, 304a, 304b is made of a non-absorbent material such as fiberglass pad, polyester, rayon or a similar material. The conjugate pad 204a, 204b, 304a, 304b is typically fabricated from a synthetic material (at least when using a gold conjugate) to ensure the efficient release of its contents.

As its name implies, the assay's detection conjugate (e.g., colloidal gold) is dried down and held in place in the conjugate pad 204a, 204b, 304a, 304b until a liquid test sample is applied to the sample pad. The liquid from the sample, by capillary action moves into the conjugate pad 204a, 204b, 304a, 304b, re-hydrates the dry conjugate and allows the mixing of the sample with the conjugate. The complex of conjugate and analyte then moves into and up the assay strip 206a, 206b, 306a, 306b. Pretreatment of the conjugate pad 204a, 204b, 304a, 304b helps to ensure the conjugate releases at the proper rate and enhances its stability. The pretreatment is performed in the same way as with the sample pad 216a, 216b, or 316.

In one embodiment, the at least one capture binding moiety 208a, 208b, 308a, 308b may be added to the test or calibration strips with a dispenser that gently slides a soft capillary tube across the membrane. A dispenser pump releases a constant volume of the reagents down the length of the membrane. This system is simple, easy to use, and low cost. They can be somewhat cumbersome in large scale manufacturing and many systems require a technician to constantly feed the nitrocellulose cards and to monitor reagent levels as well as the quality of the test and control lines.

An alternative method of applying the at least one capture binding moiety 208a, 208b, 308a, 308b includes a non-contact aerosol system. These sprayers dispense solutions in controlled ultrafine, ultra-small volume aerosols. These devices project very fine droplets of reagent onto the membrane and overlap the drops to create a continuous line. Spraying offers much more control of the reagent application, but it also adds capital expense and increases the complexity of strip manufacturing. These devices are more appropriate in very large scale manufacturing or when a reader with tight tolerances will be used to analyze the lateral flow test strips.

In the foregoing, addition of one line of the at least one capture binding moiety 208a, 208b, 308a, 308b onto each of the test or calibration strips is discussed. However, one will appreciate that a cassette 200 or 300 may include multiple test and control lines that may each be configured to interact with a different analyte of interest.

In addition to assay devices that are configured to directly detect analytes of interest on a lateral flow immune assay cassette, lateral flow cassettes can be developed for detecting analytes in interest by linking their detection to one or more enzymatic reactions.

In one example, an enzyme present in a sample may be assayed and its concentration and/or activity determined by applying the sample to a lateral flow cassette where the enzyme's substrate is immobilized to the cassette. For example, an enzyme substrate that is linked to a detectable label may be immobilized to the fluid transport matrix of a lateral flow cassette. In one embodiment, the detectable label may be cleaved from the substrate in response to enzymatic cleavage of the substrates. Prior to degradation of the substrate, the detectable label provides a first signal. In response to enzymatic cleavage of the substrate, the detectable label is lost from the line of substrate. The concentration or activity of the enzyme is calculated as a function of the loss of signal from the substrate line as a function of time.

In another embodiment, an enzyme substrate present may be detected on an assay cassette that includes an immobilized enzyme that can break down the substrate. In this instance, the substrate is not detected directly. Instead, a product of breakdown of the substrate by one or more linked enzymatic reactions is able to interact with an enzymatically activated detectable label in such a way that renders the reporter detectable.

When the sample is applied to the lateral-flow chromatographic assay cassette, the substrate, which is in the sample, diffuses through the fluid transport matrix of the lateral-flow chromatographic assay cassette where the substrate can encounter an immobilized enzyme that can degrade the substrate, producing a breakdown product. In the absence of the breakdown product, the reporter does not produce a detectable signal. In contrast, when the breakdown product interacts with the reporter, the reporter is modified, thus producing a detectable signal (e.g., phosphorescence, fluorescence, color change, etc.). The product of enzymatic breakdown of the substrate may interact directly with the reporter, or one or more additional enzymatic reactions may be linked to the first enzymatic reaction in order to produce a product that can interact with the reporter.

Suitable examples of enzymes that can be assayed using the devices and methods described herein include, but are not limited to, alanine aminotransferase, aspartate aminotransferase, amylase, lipase, gamma glutamyl transpeptidase, alkaline phosphatase, lactate dehydrogenase, acid phosphatase, aldolase, and glucose-6-phosphate dehydrogenase.

Suitable examples of enzymatic substrates that can be assayed using the devices and methods described herein include, but are not limited to, creatinine, uric acid, bilirubin, and phenylalanine, beta hydroxyl butyrate, alpha keto gluterate, lactic acid, ammonia, bicarbonate, bile acids, ethanol, glucose, cholesterol, triglycerides.

For example, an assay for creatinine may involve several linked enzymatic reactions. A method may include creatininase, creatinase, sarcosine oxidase, and a peroxidase. The hydrogen peroxide liberated in the sarcosine oxidase reaction is used by the peroxidase to produce a colored substance that can be measured spectrophotometrically or fluorimetrically. Uric acid, bilirubin, phenylalanine, and other metabolites may be detected using similar schemes.

Additional discussion of devices that can be used to perform an enzymatic assay, which may be used in one or more of the methods described herein, may be found in U.S. Prov. App. Ser. No. 61/625,390 entitled "HANDHELD DEVICE FOR PERFORMING AN ENZYME-BASED DIAGNOSTIC TEST AND METHODS FOR USE THEREOF" and filed 17 Apr. 2012, the entirety of which is incorporated herein by reference.

Referring now to FIGS. 4A and 4B, plan and side views of a diagnostic test system 240 are illustrated. In one embodiment, the diagnostic test system 240 may include a handheld device 250 and a testing apparatus 260.

In the illustrated embodiment, the handheld device 250 is an iPhone. However, the handheld 250 device can be essentially any cell phone device, digital camera device, or a similar device that has an onboard camera/image capture function, data collection and analysis capabilities, data and results display capabilities, and, preferably, the ability to communicate with one or more remote computer or cellphone networks for data upload, querying a data analysis algorithm, querying a decision support algorithm, and the like. In the illustrated embodiment, the handheld device 250 includes a front-directed camera 280, a back-directed camera (not shown) that is directed into the testing apparatus, a display screen 290, and audio input and output ports 295a and 295b. The display screen 290 can be used for display of data and results. In addition, the display screen 290 may include touchscreen capabilities that can be used for input of data or commands. Additionally the front-directed camera can be used for imaging QR and bar code information identifying the test to be performed and providing lot number, expiration date, and control values as well as other parameters as needed for test identification, calibration, results interpretation, and data reporting.

In one embodiment, the testing apparatus 260 is designed to be securely coupled to the handheld device 250. For example, the testing apparatus 260 may be designed to fit a specific class or brand of handheld devices. The testing apparatus includes a cassette port 270 that is designed to allow an assay device, such as a lateral flow immunoassay cassette 105 (see FIG. 1), to be inserted into the testing apparatus 260. Additionally, an interior portion of the testing apparatus 260 may be painted with a flat black color so as to avoid extraneous and reflected light. In addition, the testing apparatus 260 includes a number of internal components (e.g., i/o ports, power ports, light source(s), lens(es), light conducting media, etc.) that are designed to transform the handheld device 250 into a device that can be used to collect and analyze data produced by an assay device, such as the lateral flow immunoassay cassette 105 (see FIG. 1).

While the testing apparatus 260, is shown fitted to the handheld device 250, one will appreciate that they testing apparatus can be configured as a separate unit that includes its own light source, power supply, optics, data capture capabilities, and the like. In such an embodiment, the testing apparatus may be configured to collect assay data from an assay cassette and transfer it (e.g., by a wired or wireless connection, by Bluetooth™, RFID, NFC, or direct transfer via USB or the headphone jack or the like) to the handheld device for analysis and reporting.

Figure 5A:
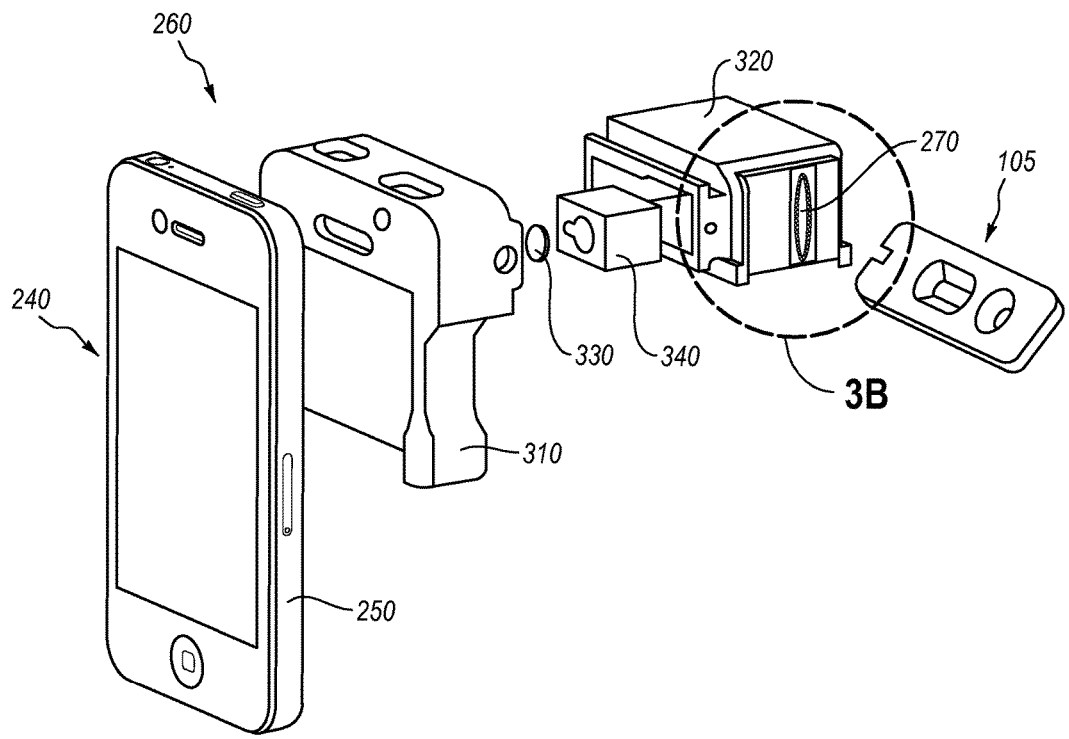
FIG. 5A illustrates an exploded view of the diagnostic testing system that is illustrated in FIGS. 4A and 4B.

Referring now to FIG. 5A, FIG. 5A illustrates an exploded view of the diagnostic testing system 240 that is illustrated in FIGS. 4A and 4B. As can be seen in the exploded view, the testing apparatus 260 includes a main body housing 310 and an assay housing 320.

The main body housing 310 is primarily designed to mate cleanly with the handheld device 250. For example, the main body housing 310 may be shaped such that the handheld device 250 can be slid into the main body housing 310 such that the handheld device 250 clicks into or otherwise securely mates with the main body housing 310. The main body housing 310 may also include one or more gaskets, seals, and the like that allow the handheld device to form a secure and light-tight seal with the main body housing 310. Additional features of the main body housing 310 will be discussed below.

The assay housing 320 is fixedly coupled to the main body housing 310. In the illustrated embodiment, the assay housing 320 includes a cassette port 270 that is configured such that a lateral flow immunoassay cassette 105 can be inserted into the assay housing 320. In addition, the assay housing 320 in the in the illustrated embodiment includes a lens that is interposed between the handheld device's 250 back-directed camera (not shown) and the lateral flow immunoassay cassette 105. Likewise, an optical fiber device or light pipe 340 that is capable of transmitting light either to the lateral flow immunoassay cassette 105 from the hand held device's 250 light source (not shown), from the lateral flow immunoassay cassette 105 to the hand held device's 250 back-directed camera (not shown), or both.

While the hand held device's 250 light source (not shown) can be used to illuminate the lateral flow immunoassay cassette 105, the diagnostic testing system 240 may also include one or more additional light sources that can be housed in either the assay housing 320 or the main body housing 310. Suitable examples of light sources can include, but are not limited to a camera flash, an autofocus illuminator on a camera, an LED light, an incandescent lamp, or a gas-discharge lamp. For example, the light source can come from micro-LED lamps that are included in the assay housing 320. The micro-LEDs can be selected to emit certain wavelengths that are adapted for one or more assay conditions. The micro-LEDs can be powered by drawing electrical power from the battery of the handheld device 250. In addition, either the assay housing 320 or the main body housing 310 may be configured such that ambient light or sunlight can be used to illuminate the lateral flow immunoassay cassette 105.

In one embodiment, at least one wavelength filter may be interposed between the light source and the lateral-flow chromatographic immunoassay cassette 105. For example, if the assay is a fluorescent assay, then the wavelength filter may be used to yield a specific wavelength of light from the light source to excite fluorescent emission from the assay system. Likewise, certain colored dyes may yield a better signal when excited by selected wavelengths of light. Additional filters may be positioned in front of imaging device to perform, for example, Raman spectroscopy.

In one embodiment, the lens 330 (e.g., a collimating lens) may be used for focusing the light source on the lateral-flow chromatographic immunoassay cassette 105. For example, the lens 330 may be used to increase the amount of incident light impinging on the lateral-flow chromatographic immunoassay cassette 105. For instance, the purpose of the lens 330 may be to bring the focal point of the camera of the handheld device 250 (which is limited to about 6 inches or more) to less than 2 centimeters. This allows for a smaller overall package and produces a finer image that prevents the use of convoluting a blurry picture using Fourier transforms in order to produce a usable data that can be analyzed. Furthermore, with a multi-analyte detection assay (e.g., two calibration standard lines and a test sample line), the finer image will prevent overlap of the target lines to improve sensitivity and accuracy. In another example, a focusing apparatus may be used to focus ambient light or sunlight on the analysis zone of the lateral-flow chromatographic immunoassay cassette 105.

In some embodiments, the assay cover 320 may include a device that can allow the angle of the lateral-flow chromatographic immunoassay cassette 105 to be adjusted relative to the handheld device 250 and a light source (not shown). By selectively modifying these angles, the lower detection limit of the assay can be extended, the signal to noise ratio can be improved, etc. In one embodiment, the device can be adjusted manually in order to choose an angle that optimizes detection limit, signal to noise, and the like. In another embodiment, the device can be coupled to a mechanical means, such as a servo motor or a gel-damped spring device that can allow the device to automatically sample a number of angles while the handheld device 250 collects data from the lateral-flow chromatographic immunoassay cassette 105.

Figure 5B:
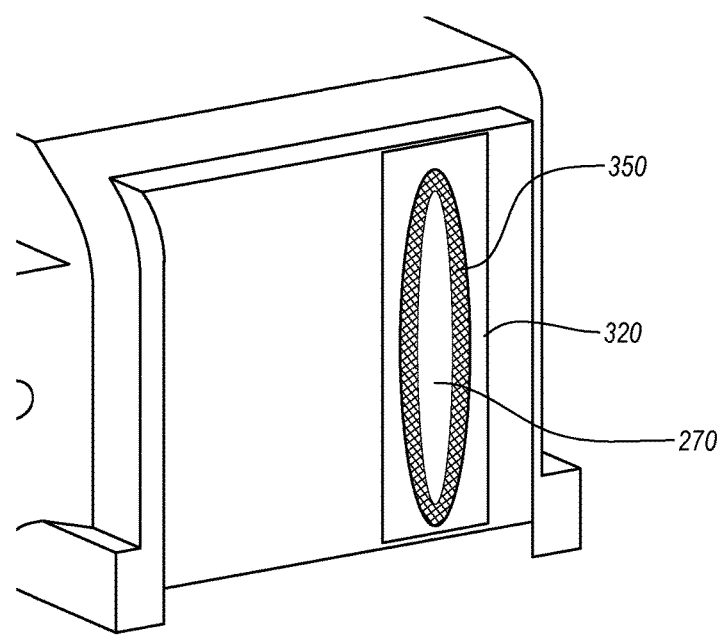
FIG. 5B illustrates a view of a component of the diagnostic test system shown in FIG. 5A, wherein the component includes a light sealing feature.

Referring now to FIG. 5B, the assay housing 320 and the cassette port 270 are illustrated in greater detail. In the embodiment illustrated in FIG. 3B, the cassette port 270 of the assay housing 320 includes a sealing gasket 350 disposed around the cassette port 270 that can seal the cassette port 270 when an assay cassette 105 is inserted therein so that ambient light does not leak into the housing 260. For example, if ambient light leaks into the housing 260, it could skew results. In addition, the cassette port 270 may include a spring-loaded flap (not shown) or similar means that can seal ambient light out of the housing 260 even when no cassette 105 is inserted into the cassette port 270.

Figure 6:
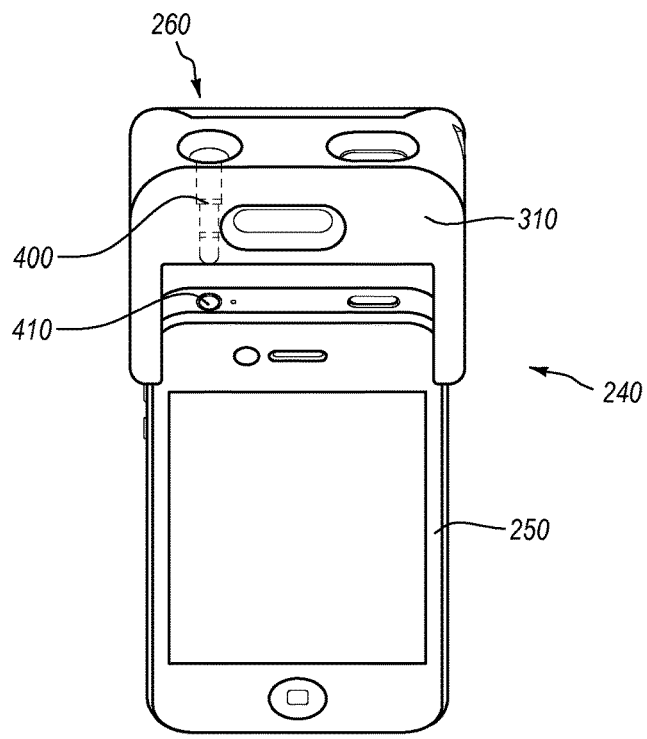
FIG. 6 illustrates a view of a diagnostic test system that includes an indexing feature for aligning the digital camera device and the testing apparatus.
Figure 7A:
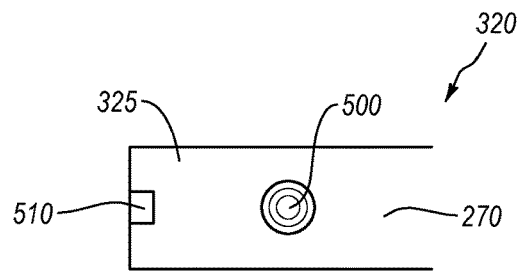
FIG. 7A is a cut-away view of a testing apparatus of a diagnostic test system illustrating a target device configured for normalizing and/or calibrating the light source and the detector of the diagnostic test system.
Figure 7B:
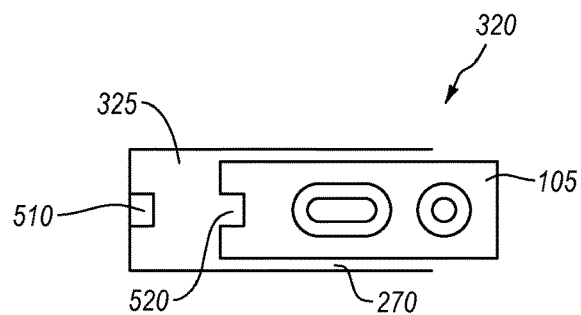
FIG. 7B is a cut-away view of a testing apparatus of a diagnostic test system illustrating a mechanical interlock feature configured to interlock with a corresponding second mechanical interlock feature on a lateral-flow chromatographic assay cassette.

Referring now to FIGS. 6, 7A, and 7B, additional features of the housing 260 are illustrated.

Referring to FIG. 6, an example of an indexing feature that can reliably align the housing 260 relative to the handheld device 250 is illustrated. In the illustrated embodiment, the indexing feature may include a headphone jack 410 that is integrated into the housing body 310. When the handheld device 250 is inserted into the housing body 310, the headphone jack 400 is positioned such that it can be inserted into the headphone port 410 of the handheld device 250. It will be understood by persons having ordinary skill in the art that headphone jack 400 is but one example of an indexing feature and that additional indexing features can be employed without departing from the spirit of this discussion.

In addition to aligning the housing body 310 relative to the handheld device 250, the headphone jack 400 can be used to draw electrical power from the handheld device 250 in order to power components (e.g., one or more illumination devices) that are positioned in the housing 260. Likewise, the headphone jack 400 can be used for data transfer between the handheld device 250 and components in the housing 260.

Referring now to FIG. 7A, a target device 500 is illustrated. The target device 500 can be used to normalize/calibrate the response of at least one of the camera or the light source of the handheld device. In one embodiment, the target device may located on an interior surface 325 of the assay housing 320 in close proximity to the cassette port 270 in an area that is can be illuminated by a light source that will be employed for illumination of an assay cassette and viewable by a camera of a handheld device that is going to be used to capture data from the cassette. For example, the target device may have a known color and/or color intensity that can give a known response for calibrating the light source and the camera. In addition, the target device 500 can be used to ensure that the light source and the camera are directed at the proper point when the handheld device in inserted into the housing.

Referring now to FIGS. 7A and 7B, the assay housing 320 may further include a mechanical interlocking feature 510 that is positioned and configured to mate with a mechanical interlocking feature 520 on the assay cassette. For example, the mechanical interlocking features 510 and 520 may include tab and cut-out features that are designed to fit together. Such mechanical interlocking features 510 and 520 may be used to ensure that the cassette 105 is inserted in to the assay housing 320 in the proper orientation. In addition, such mechanical interlocking features 510 and 520 may be coupled to a disabling feature that can shut down the device if an incompatible cassette is inserted into the housing 320 or if the cassette is inserted in the wrong orientation. This can, for example, be an important safety feature because it prevents the device from reading the wrong portion of the cassette and giving an erroneous reading as a result.

Methods for Detecting at Least One Analyte of Interest in a Sample

In one embodiment, a method for detecting at least one analyte of interest (e.g., a biometric analyte) in a sample is disclosed. The method includes providing a lateral-flow chromatographic assay cassette and providing a testing device that is capable of interfacing with the lateral-flow chromatographic assay cassette.

In an embodiment, the lateral-flow chromatographic assay cassette may include a capture ligand capable of capturing and localizing at least one analyte of interest in a sample on an analysis surface of the lateral-flow chromatographic assay cassette, at least one reporter configured for interacting with at least one of the analyte of interest or the capture ligand, and at least a first calibration standard and a second calibration standard configured to provide at least a two-point calibration curve. In another embodiment, a lateral-flow chromatographic assay cassette may include an absorbent test strip for analyzing an analyte of interest in an experimental sample and an absorbent calibration strip for running at least one calibration standard positioned in proximity to the absorbent test strip as described in greater detail elsewhere herein.

Figure 8:
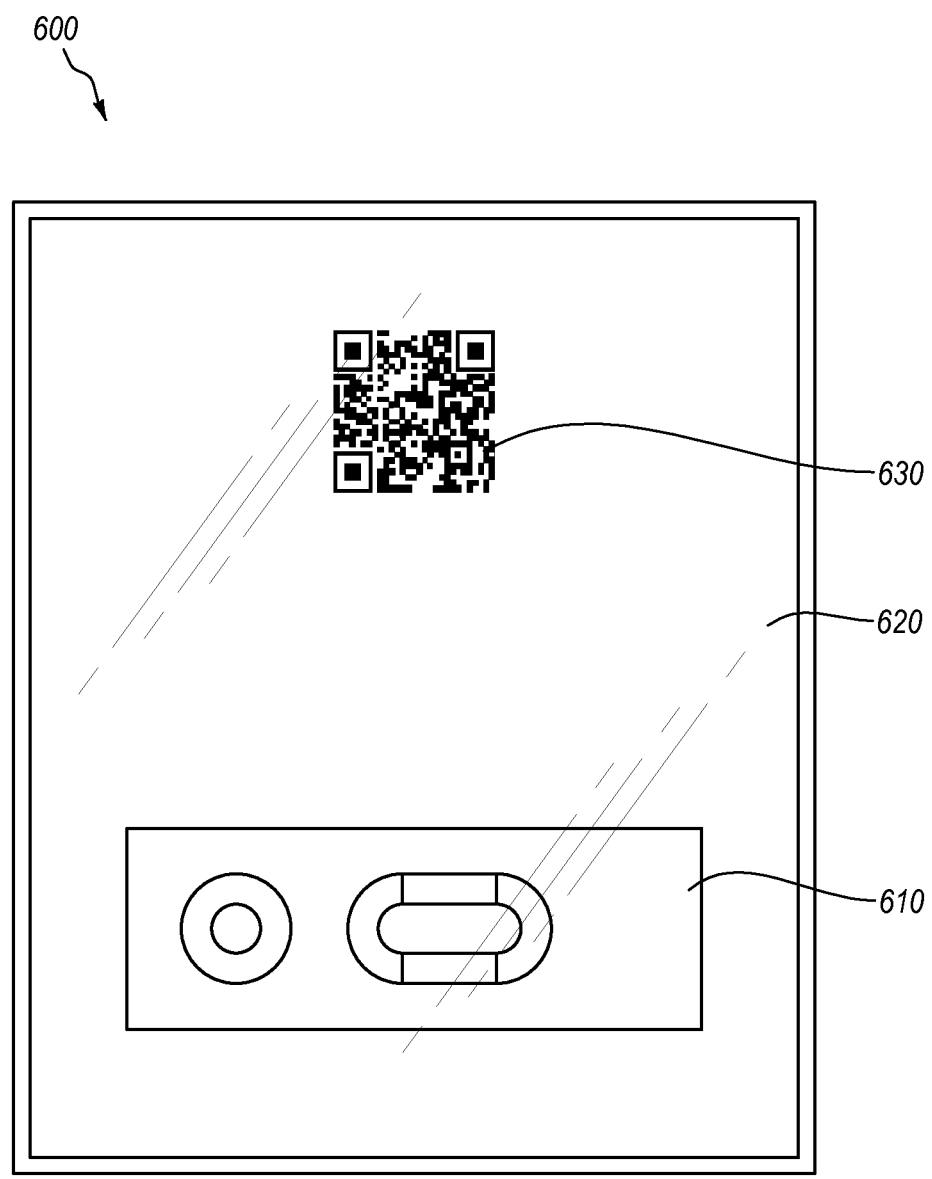
FIG. 8 illustrates a lateral-flow chromatographic assay cassette packaging system that includes a tracking feature readable by the handheld device.

In one embodiment, the lateral-flow chromatographic assay cassette may be packaged in a packaging system 600, as illustrated in FIG. 8. The packaging system 600 includes a sealed package (e.g., a plastic-, foil-, or paper-based package) that can be used for containing, storing, or transporting the lateral-flow chromatographic assay cassette 610 in a clean and preferably sterile environment. A QR code decal or sticker with relevant cassette information could be applied or printed to the outside of each foil pouch or canister.

In addition, the packaging system 600 includes a tracking code 630. In the illustrated embodiment, the tracking code 630 is a QR code, which is a two-dimensional bar code. Two-dimensional bar codes, like QR codes, can be used to store far more information that can be stored in a conventional bar code. For example, a QR code can be used to store up ~4300 alphanumeric characters (i.e., 0-9, A-Z, space, $, %, *, +, −, ., /, :, etc.). In one embodiment, the tracking code 630 can be read by the diagnostic testing system prior to initiating a test. The tracking code may be used to store information that is relevant to the test in a format that can be read by the device. For example, the tracking code 630 can be used for recording and then transmitting to the test system the values for the calibration standards used on the lateral-flow chromatographic assay cassette 610, manufacturer, date of manufacture, lot number for the lateral-flow chromatographic assay cassette 610, manufacturer, date of manufacture, and sample/results tracking.

The testing device may include a testing apparatus that is configured to couple the lateral-flow chromatographic assay cassette to the handheld device in proximity to a light source, the light source being capable of transmitting at least one wavelength of light configured to yield a detectable signal from the reporter(s) (e.g., at least one reporter configured for interacting with at least one of the analyte of interest in a test sample and/or a calibration sample, the first calibration standard, and the second calibration standard), and a detector is positioned to capture the detectable signal from the reporter(s).

The method may further include applying a liquid sample that includes at least one analyte of interest to the lateral-flow chromatographic assay cassette. In some embodiments, applying a liquid sample to the cassette may include applying separate test and calibration samples to separate test and calibration strips. The method may further include inserting the lateral-flow chromatographic assay cassette into the testing apparatus device, illuminating the lateral-flow chromatographic assay cassette with the light source of the testing device in order to yield a detectable signal from the reporter(s), and querying an interpretive algorithm for (i) calculating the calibration curve and then (ii) converting the detectable signal from the first reporter to a numerical value related to the presence or amount of the at least one analyte present in a sample.

In one embodiment, the calibration curve may be calculated based on values from interaction of a first calibration standard and a second calibration standard with calibration standard lines on the cassette. See, e.g., calibration standards lines 150a and 150b of FIG. 1. In another embodiment, the calibration curve may be calculated based on (1) observing a blank region of the absorbent calibration strip, and (2) generating a two point calibration curve that includes a value for the interaction of the analyte of interest from the liquid calibration standard with the ligand immobilized on the absorbent calibration strip and a value for the blank region of the absorbent calibration strip. An example of the blank region on a calibration strip 206*b* and 306*b* is illustrated at 222 and 322 in FIGS. 2A and 3A. Because the calibration strip may not be pure white, the strip may produce a background signal that needs to be subtracted to get a true value for the signal from the test and calibration lines. Moreover, instead of assuming a zero value, observing the background signal in the blank region allows the calculation of a true two-point calibration curve, which is more accurate.

In one embodiment, the method may further include providing means for dispensing a known amount of liquid from a sample pad of the assay cassette. Such means may include, without limitation, rollers, presses, rollers or presses that include a stop that determines how much liquid can be squeezed from the samples pad, spring loaded devices that automatically press down on the sample pad to dispense a predetermined amount of liquid, and the like. In one embodiment, the testing device may include means for dispensing a known amount of liquid from the sample pad. For example, the testing device may include a port for inserting the lateral-flow chromatographic assay cassette into the testing device. Such a port may, for example, include a roller or a similar means that rolls over the sample pad and dispenses a selected amount of liquid therefrom when the cassette is inserted into the testing device.

In one embodiment, a single immunoassay device may contain multiple types of different capture moieties (e.g., antibodies) each conjugated with different dyes (e.g., quantum dots) and/or multiple capture bands each immobilized with different capture moieties. A single light source (e.g., an ultraviolet light) illuminates all dyes (e.g., quantum dots) simultaneously, and the detector device (e.g., a digital camera) captures the emitted signals from multiple bands simultaneously.

In one embodiment, analytes of interest assayed on the lateral flow immunoassay cassettes described herein may be detected and quantified by elastic light scattering. The amount of light scattered from a selected region of a lateral flow immunoassay cassette (e.g., a capture band) is highly sensitive to the amount of material in a region illuminated by an incident light. In general, elastic light scattering, coupled with angle optimization, may be as much as 100 times more sensitive than comparable reflectance or fluorescence analysis. Other excitation/detection methods may include surface plasmon detection; Rayleigh scattering, reflectance, diffuse scattering, electrochemical detection, conductivity, fluorescence, magnetic, enzymatic, transmission, absorbtion, acoustic detection, any other method which is based upon Beer's law, kinetic analysis (e.g., change in signal strength over time), and the like.

In one embodiment, a light source may be positioned at a certain angle to the lateral flow assay cassette and the detector (e.g., a detection fiber or a cell phone camera) or fiber (eventually the cellphone camera CCD). In one embodiment, the reporter(s) may be queried by taking a reading from each reporter and calculating the intensity of the scattered light. Signal intensity (i.e., the amount of scattered light that is detected) decreases as the concentration of the analyte of interest increases.

In an embodiment that includes a cell phone camera or the like, the camera's CCD will take an image. In one embodiment, the image may be taken with a red distance filter. In the image, the calibration standard lines and the test lines will be present. The digital image will then undergo digital image processing with a selected digital processing algorithm to produce a representative image of the color bands for the calibration standard lines and test simultaneously. For example, a digital processing algorithm may (1) identify the areas of interest (e.g., the test line and the at least two calibration standard lines) in the image taken of the lateral flow immunoassay cassette, (2) calculate an RGB value for each pixel in the image, (3) convert RGB format to xyz format, (4) convert xyz format to Lab color format, (5) assign a numerical value to each of the areas of interest (e.g., the test line and the at least two calibration standard lines), (6) calculate a calibration curve based on the numerical values obtained from the first and second calibration standard lines values, and (7) convert the numerical value for the test line into a concentration value for the analyte of interest in the sample.

In addition, internal controls, such as but not limited to, a control line (e.g., a fluorescent marker) to potentially eliminate or reduce variations in the final signal from manufacturing tolerances of the lateral flow assay cassette may be used to increase the robustness and reliability of the analysis. Additionally, analysis of the white portion of the lateral flow assay cassette may be used as an additional negative control to further improve reproducibility.

Figure 9:
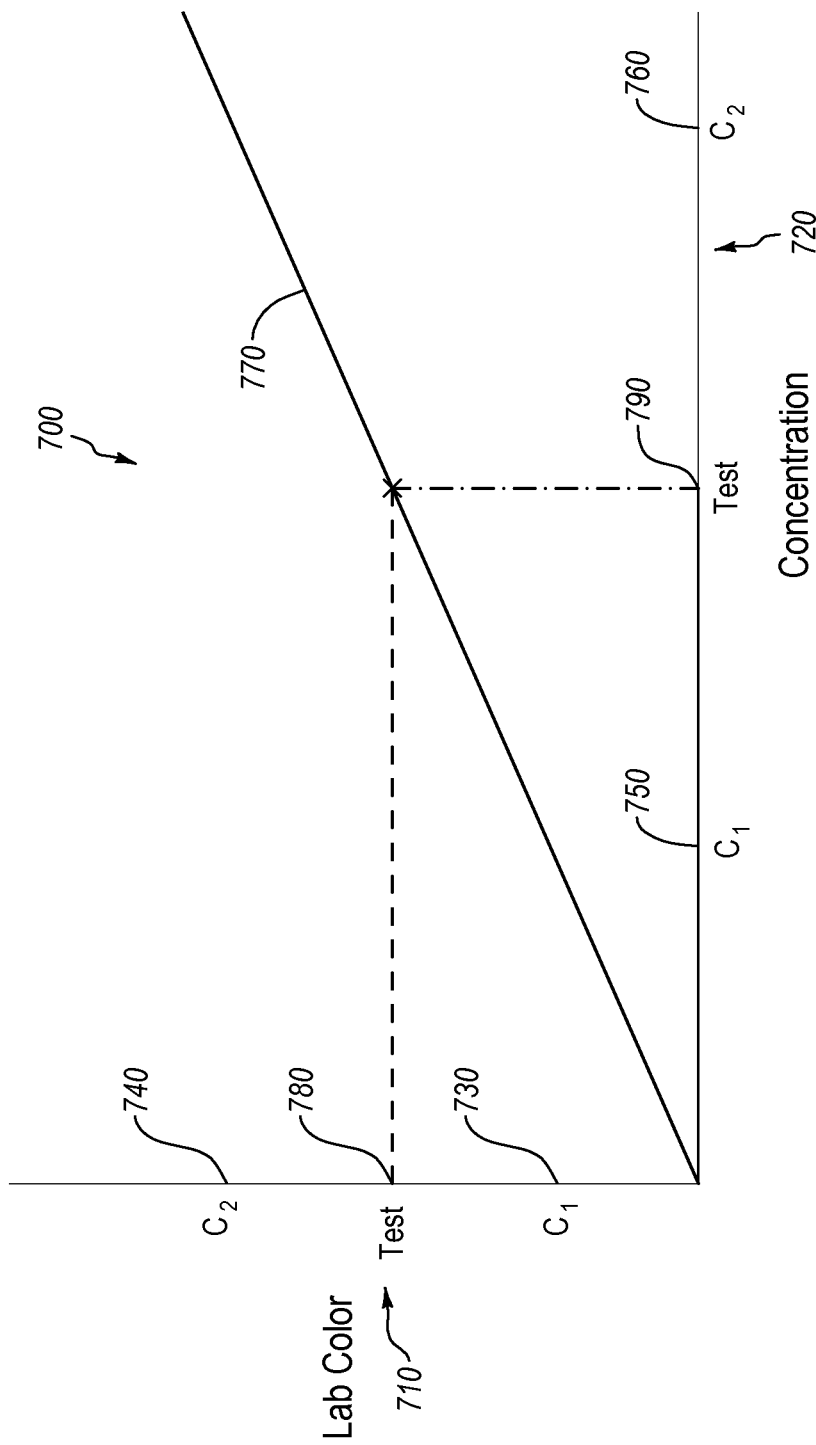
FIG. 9 illustrates a two point calibration curve according to one embodiment of the present disclosure.

The digital processing algorithm is able to convert the numerical value for the test line into a concentration value because the at least two calibration standard lines are selected to provide numerical values that are proportional to non-zero concentration amounts for the analyte of interest. This relationship is clarified by reference to FIG. 9, which shows a graph 700 with Lab value on the Y-axis and concentration on the X-axis. The first and second calibration standards have a known response that relates to known and, preferably, non-zero concentration values for the analyte of interest. Lab values for each of the first and second calibration standards 730 and 740 can be related to a concentration for each 750 and 760 by a simple relationship. By relating observed Lab color values to concentration values 750 and 760, a calibration curve 770 can be generated that can be used to calculate the concentration 790 of the analyte of interest in the sample based on the observed Lab color 780. One will of course appreciate that the calibration curve 770 can also be described by a mathematical formula and that the analysis algorithm may not actually generate a calibration curve, per se.

In one embodiment, the method may further include mixing the liquid sample with a dye conjugate prior to applying the sample to the lateral-flow chromatographic immunoassay cassette. In one embodiment, the dye conjugate is configured to interact with at least one of the analyte of interest or the ligand to provide a visual readout related to the presence or concentration of the analyte of interest in the sample. In one embodiment, the sample includes at least one control substance and at least one analyte of interest.

In one embodiment, the observation of the interaction of the at least one analyte of interest with the at least one ligand immobilized on the lateral-flow chromatographic immunoassay cassette may be timed by observing the appearance of at least one control substance. For example, an assay may be read ~10 minutes after a diluent is applied. By monitoring the position of the wave front or the appearance of the control line, it may be possible to eliminate the need to manually time the test. Likewise, by observing the timing of the appearance of a control, the most favorable time for reading the assay can be identified. These could include monitoring the movement of the mobile phase, monitoring the movement of the control substance, timing the movement of the mobile phase, taking sequential images of the test result, detecting when buffer is added, detecting when liquid has traveled the length of the membrane, and combinations thereof.

In addition, testing device may include or may be configured to access an interpretive algorithm stored in a computer readable format and electronically coupled to the handheld device, wherein the interpretive algorithm is configured to (i) calculate a calibration curve based on the first calibration standard and the second calibration standard and then (ii) convert the detectable signal from the first reporter to a numerical value related to the presence or amount of the at least one analyte present in a sample. The interpretive algorithm may be included in an on-board computing system of the handheld device or the interpretive algorithm may be stored remotely in a computer storage medium that is accessible by the handheld device.

In one embodiment, the interpretive algorithm queried in the above described method may include one or more computer storage media having stored thereon computer executable instructions that, when executed by one or more processors of the detector device, implement a method for interpreting the numerical value related to the presence or amount of the at least one analyte present in the sample. In one embodiment, the computer implemented method may include (1) receiving a user initiated request to convert the visual signal readout of the immunoassay apparatus to a numerical value, (2) in response to the request, an act of identifying at least one visual signal readout of the immunoassay apparatus, (3) capturing at least one digital signal from the at least one visual signal readout of the immunoassay apparatus, (4) converting the at least digital signal to at least one numerical, and (5) using the at least one numerical value to determine an amount or concentration of at least one analyte present in the sample. This numerical value can then be displayed on a screen located on the detector device and/or stored, interpreted, or sent to a database.

In one embodiment, the computer implemented method may further include at least one of: (1) communicating with an electronic medical records system via a wireless communication channel, (2) uploading the amount or concentration of the at least one analyte present in the sample to the electronic medical records system, or (3) querying a decision support algorithm, wherein the decision support algorithm uses the at least one numerical value to support a diagnosis of at least one condition in a subject and to suggest a course of treatment.

Embodiments of the present disclosure may comprise or utilize special purpose or general-purpose computing devices that include computer hardware, such as, for example, one or more processors and system memory, as discussed in greater detail below. Embodiments within the scope of the present invention also include physical and other computer-readable and recordable type media for carrying or storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from mere transitory carrier waves.

Computer-readable media that carry computer-executable instructions are transmission media. Thus, by way of example, and not limitation, embodiments of the invention can comprise at least two distinctly different kinds of computer-readable recordable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with mobile consumer computing devices. Mobile consumer computing devices or more simply, mobile consumer devices, can be any of a broad range of computing devices designed or optimized for portability and for personal use. Mobile consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE IPAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many mobile consumer devices are expandable, such that a user can add new hardware and functionality not present during manufacture of the device. It will be appreciated that as the market for mobile consumer devices expands and develops, the functionality of these devices will also expand to utilize new and improved user-interaction devices and communications devices. The embodiments described herein are expansive and can also utilize any future developments in the field of mobile consumer devices.

Further discussion of lateral flow assay devices can be found in U.S. Prov. Pat. App. Ser. No. 61/533,959 filed 13 Sep. 2011, U.S. patent application Ser. No. 13/612,293 filed 12 Sep. 2012, U.S. patent application Ser. No. 14/070,276 filed 1 Nov. 2013, U.S. Prov. App. Ser. No. 61/740,975 filed 21 Dec. 2012, U.S. Prov. Pat. App. Ser. No. 61/625,368 filed 17 Apr. 2012, U.S. patent application Ser. No. 13/862,176 filed 12 Apr. 2013, U.S. Prov. Pat. App. Ser. No. 61/625,390 filed 17 Apr. 2012, and U.S. patent application Ser. No. 13/862,184 filed 12 Apr. 2013, the entireties of which are incorporated herein by reference. In addition, discussion of electro-optical devices that can be used, for example, to read, quantify, and report the results provided by such lateral flow assay devices, which may be used in one or more of the methods described herein, may be found in U.S. Prov. Pat. App. Ser. No. 61/533,959 filed 13 Sep. 2011, U.S. patent application Ser. No. 13/612,293 filed 12 Sep. 2012, U.S. patent application Ser. No. 14/070,276 filed 1 Nov. 2013, U.S. Prov. App. Ser. No. 61/740,975 filed 21 Dec. 2012, U.S. Prov. Pat. App. Ser. No. 61/625,368 filed 17 Apr. 2012, U.S. patent application Ser. No. 13/862,176 filed 12 Apr. 2013, U.S. Prov. Pat. App. Ser. No. 61/625,390 filed 17 Apr. 2012, and U.S. patent application Ser. No. 13/862,184 filed 12 Apr. 2013.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for monitoring and adjusting a biometric, comprising
    providing a portable monitoring apparatus configured to monitor a selected biometric analyte, wherein the monitoring apparatus includes:
        an assay apparatus configured for providing a detectable signal in response to an amount of the selected biometric analyte in a sample, wherein the assay apparatus is a lateral-flow chromatographic assay cassette having at least one ligand immobilized thereon configured for capturing the selected biometric analyte in the sample;
        a light source that is positioned to illuminate the assay apparatus with at least one wavelength of light capable of interacting with the assay apparatus and the selected biometric analyte to produce the detectable signal, wherein the light source is located on one side of the assay apparatus;
        a detector device that is positioned to capture the detectable signal from the assay apparatus, wherein the detector is one of a handheld digital camera device, a camera phone, a smart phone, or a tablet computer;
        a sample holder configured to couple the assay apparatus to the detector device in relation to the detector device and the light source;
        a collimating lens positioned between the detector device and the assay apparatus to change a focal length of the detector device such that the assay apparatus can be imaged by the detector device; and
        an interpretive algorithm stored in a computer readable format and electronically coupled to the detector device, wherein the interpretive algorithm is configured to convert the detectable signal to a numerical value related to the amount of the selected biometric analyte in the sample; and
    monitoring the selected biometric analyte associated with the biometric to define a state of the biometric in a subject having one or more physiological parameters defined by one or more of the biometrics, wherein the selected biometric analyte is serum osmolarity (tears), based on the results of the monitoring, adjusting the state of the biometric at the point of care by administering to the subject a supplement selected to affect the state of the biometric.

2. The method of claim 1, wherein the supplement is formulated for one or more of (1) oral administration, (2) intranasal administration, (3) transmucosal administration, (4) parenteral injection, (5) implant for sustained release, (6) transdermal patch, or (7) topical administration.

3. The method of claim 1, wherein the selected biometric analyte is used to adjust the dosing of the supplement.

4. The method of claim 1, wherein the selected biometric analyte is used to select one or more supplements based on the results of the monitoring.

5. The method of claim 1, wherein the supplement is selected from the group consisting of one or more of:
  i. *Cissus quadrangularis* and phosphotidylserine and one or more of valerian, Siberian ginseng, *Schisandra chinensis*, panax ginseng, *Rhodiiola rosea*, Vitamin C, hops, brazil nuts, English walnuts, fish oil, lettuce, or one or more extracts thereof
  ii. red yeast rice extract, T2;
  iii. strontium, vitamin D3, Ca, Mg, vitamin K, and *Cissus quadrangularis;*
  iv. iron, folic acid, vitamin B12;
  v. iodine, selenium;
  vi. saw palmetto;
  vii. evening primrose;
  vii. phytoestrogens, black cohosh;
  ix. water;
  x. pregnancy vitamins, lepidium meyenii, mucuna pruriens;
  xi. vitamins, lepidium meyenii, mucuna pruriens;
  xii. phlorizin, glucuronidase inhibitors, glucose;
  xiii. acetyl carnitine, sulfurphorane;
  xiv. eyebright, vitamin A, blueberry;
  xv. light therapy, melatonin, rhodiola rosea;
  xvi. pau 'arc, siberian ginseng, schisandra chinensis, panax ginseng, rhodiiola rosea;
  xvii. caffeine, acetyl carnitine;
  xviii. glucose, acetyl coA;
  xix. acetyl carnitine;
  xx. vitamin D;
  xxi. vitamin E;
  xxii. vitamin C;
  xxiii. vitamin A;
  xxiv. beta carotene;
  xxv. antioxidants;
  xxvi. estrogen and/or phytoestrogen;
  xxvii. calcium, vitamin D;
  xxviii. milk thistle;
  xxix. water, dandelion, ginger, juniper; or
  xxx. one or more of curcumin and derivatives thereof, liposomal curcumin, encapsulated curcumin, Pau D'arco, siberian ginseng, *Schisandra chinensis*, panax ginseng, *Rhodiiola rosea*, omega 3 EFA, white willow bark, green tea extract, pycneogenol, *Bogwellia serrata* resin, resveratrol, *Uncaria tomantosa, Uncria guianensia*, capsaicin, *Harpagophytm procumbens*, olive extract / olive oil, or one or more extracts thereof or pharmaceutical derivatives thereof.

* * * * *